US009453042B2

(12) United States Patent
Pereira et al.

(10) Patent No.: US 9,453,042 B2
(45) Date of Patent: Sep. 27, 2016

(54) PROCESS FOR THE PREPARATION OF MACROLIDE ANTIBACTERIAL AGENTS

(75) Inventors: David E. Pereira, Apex, NC (US); Manish Kanchanbhai Patel, Toronto (CA); Keshav Deo, Vadodara (IN)

(73) Assignee: CEMPRA PHARMACEUTICALS, INC., Chapel Hill, NC (US)

( * ) Notice: Subject to any disclaimer, the term of this patent is extended or adjusted under 35 U.S.C. 154(b) by 0 days.

(21) Appl. No.: 12/739,652

(22) PCT Filed: Oct. 23, 2008

(86) PCT No.: PCT/US2008/080936
§ 371 (c)(1),
(2), (4) Date: Apr. 23, 2010

(87) PCT Pub. No.: WO2009/055557
PCT Pub. Date: Apr. 30, 2009

(65) Prior Publication Data
US 2010/0216731 A1 Aug. 26, 2010

Related U.S. Application Data

(60) Provisional application No. 60/982,446, filed on Oct. 25, 2007.

(51) Int. Cl.
C07H 17/08 (2006.01)

(52) U.S. Cl.
CPC ..................... C07H 17/08 (2013.01)

(58) Field of Classification Search
CPC ......................................... C07H 17/08
USPC ......................................... 536/7.4
See application file for complete search history.

(56) References Cited

U.S. PATENT DOCUMENTS

| 1,354,753 A | 10/1920 | Howard |
| 3,843,787 A | 10/1974 | Fabrizio |
| 4,312,866 A | 1/1982 | Caruso |
| 4,331,803 A | 5/1982 | Watanabe et al. |
| 4,474,768 A | 10/1984 | Bright |
| 4,742,049 A | 5/1988 | Baker et al. |
| 4,886,792 A | 12/1989 | Djokic |
| 4,990,602 A | 2/1991 | Morimoto |
| 5,211,955 A | 5/1993 | Legros |
| 5,444,051 A | 8/1995 | Agouridas et al. |
| 5,527,780 A | 6/1996 | Agouridas et al. |
| 5,543,400 A | 8/1996 | Agouridas et al. |
| 5,635,485 A | 6/1997 | Agouridas et al. |
| 5,656,607 A | 8/1997 | Agouridas et al. |
| 5,747,467 A | 5/1998 | Agouridas et al. |
| 5,760,233 A | 6/1998 | Agouridas et al. |
| 5,770,579 A | 6/1998 | Agouridas et al. |
| 5,834,428 A | 11/1998 | Drucker |
| 5,985,844 A | 11/1999 | Heck |
| 6,011,142 A | 1/2000 | Bonnet et al. |
| 6,020,521 A | 2/2000 | Randolph |
| 6,028,181 A | 2/2000 | Or et al. |
| 6,096,714 A | 8/2000 | Agouridas et al. |
| 6,121,432 A | 9/2000 | Bonnet et al. |
| 6,270,768 B1 | 8/2001 | OConnell |
| 6,313,101 B1 | 11/2001 | Denis |
| 6,395,300 B1 | 5/2002 | Liang |
| 6,395,710 B1 | 5/2002 | Chu et al. |
| 6,407,074 B1 | 6/2002 | Bronk et al. |
| 6,407,257 B1 | 6/2002 | Agouridas et al. |
| 6,420,535 B1 | 7/2002 | Phan et al. |
| 6,437,106 B1 | 8/2002 | Stoner et al. |
| 6,440,941 B1 | 8/2002 | Denis |
| 6,455,505 B2 | 9/2002 | Agouridas et al. |

(Continued)

FOREIGN PATENT DOCUMENTS

| CN | 1354753 | 6/2002 |
| CN | 101045063 | 10/2007 |

(Continued)

OTHER PUBLICATIONS

International Search Report Written Opinion for PCT/US2008/080936 completed Dec. 8, 2008.
LeMahieu, R. A. et al., "Glycoside Cleavage Reactions on erythromycin A. Preparation of Erythronolide A", Journal of Medicinal Chemistry, vol. 17, No. 9, 1974, 953-956.
Romero et al., "An efficient entry to new sugar modified ketolide antibiotics" Tetrahedron Letters, vol. 46, 2005, pp. 1483-1487.
Birkenmeyer, R. D., et al. "Synthesis and Antibacterial Activity of Clindamycin Analogues: Pirlimycin, a Potent Antibacterial Agent", Journal of Medicinal Chemistry, vol. 27, No. 2, 1984, 216-223.

(Continued)

*Primary Examiner* — Layla Berry
(74) *Attorney, Agent, or Firm* — Brannon Sowers & Cracraft PC

(57) ABSTRACT

Described herein are processes for the preparation of compounds of formula (I):

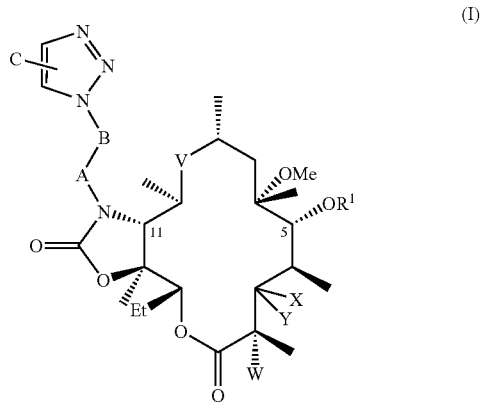

and pharmaceutically acceptable salts, solvates, and hydrates thereof.

25 Claims, No Drawings

(56) References Cited

U.S. PATENT DOCUMENTS

| | | |
|---|---|---|
| 6,515,116 B2 | 2/2003 | Suh |
| 6,555,524 B2 | 4/2003 | Kaneko |
| 6,664,238 B1 | 12/2003 | Su et al. |
| 6,777,393 B2 | 8/2004 | Bronk |
| 6,809,188 B1 | 10/2004 | Suh |
| 6,849,608 B2 | 2/2005 | Su |
| 6,890,907 B2 | 5/2005 | Speirs et al. |
| 7,163,924 B2 | 1/2007 | Burger |
| 7,332,476 B2 | 2/2008 | Burger |
| 7,375,234 B2 | 5/2008 | Sharpless |
| 7,419,961 B2 | 9/2008 | Napoletano |
| 7,601,695 B2* | 10/2009 | Liang et al. .................. 514/29 |
| 8,247,394 B2 | 8/2012 | Fernandes |
| 8,791,080 B2 | 7/2014 | Fernandes |
| 8,796,232 B2 | 8/2014 | Fernandes |
| 2002/0028781 A1 | 3/2002 | Agouridas et al. |
| 2002/0044967 A1 | 4/2002 | Yamashita |
| 2003/0143162 A1 | 7/2003 | Speirs |
| 2003/0176327 A1 | 9/2003 | Cassell |
| 2004/0009930 A1 | 1/2004 | Su |
| 2004/0014685 A1 | 1/2004 | Mercep |
| 2005/0009764 A1* | 1/2005 | Burger et al. .................. 514/29 |
| 2005/0014706 A1 | 1/2005 | Falzari |
| 2005/0022242 A1 | 1/2005 | Rosetti et al. |
| 2005/0153905 A1 | 7/2005 | Burger et al. |
| 2005/0209172 A1 | 9/2005 | Woo |
| 2005/0222427 A1 | 10/2005 | Sharpless et al. |
| 2006/0100164 A1 | 5/2006 | Liang et al. |
| 2006/0264385 A1 | 11/2006 | Wang |
| 2007/0015719 A1 | 1/2007 | Jenkins |
| 2007/0167382 A1 | 7/2007 | Finkelstein |
| 2007/0197518 A1 | 8/2007 | Johnson |
| 2007/0281894 A1 | 12/2007 | Gant |
| 2008/0113926 A1 | 5/2008 | Ivezic |
| 2008/0221048 A1 | 9/2008 | Woo |
| 2008/0227730 A1 | 9/2008 | Mutak |
| 2008/0241959 A1 | 10/2008 | Culic |
| 2008/0287376 A1 | 11/2008 | Das |
| 2009/0075916 A1 | 3/2009 | Upadhyay |
| 2009/0076253 A1 | 3/2009 | Kashimura |
| 2009/0087389 A1 | 4/2009 | Leonard |
| 2009/0156517 A1 | 6/2009 | Zhang |
| 2010/0216731 A1 | 8/2010 | Pereira |
| 2011/0195920 A1 | 8/2011 | Fernandes |
| 2012/0071429 A1 | 3/2012 | Duffield |
| 2012/0172323 A1 | 7/2012 | Fernandes |
| 2013/0011453 A1 | 1/2013 | Latta |
| 2013/0018008 A1 | 1/2013 | Pereira |
| 2013/0045937 A1 | 2/2013 | Pereira |
| 2013/0053362 A1 | 2/2013 | Castro |
| 2013/0164351 A1 | 6/2013 | Fernandes |
| 2013/0172280 A1 | 7/2013 | Pereira |
| 2013/0345410 A1 | 12/2013 | Liang |
| 2014/0088062 A1 | 3/2014 | Pereira |
| 2014/0148431 A1 | 5/2014 | Patel |

FOREIGN PATENT DOCUMENTS

| | | |
|---|---|---|
| EP | 0248279 | 12/1987 |
| EP | 0680967 A1 | 11/1995 |
| EP | 0012521 A1 | 3/2000 |
| EP | 1024145 A2 | 8/2000 |
| EP | 1167375 | 1/2002 |
| GB | 891817 | 3/1962 |
| JP | 2000507573 | 6/2000 |
| JP | 2000351794 | 12/2000 |
| JP | 2002514197 | 5/2002 |
| JP | 2004502736 | 1/2004 |
| JP | 2006528667 | 12/2006 |
| JP | 2007536371 | 12/2007 |
| JP | 2008519788 | 6/2008 |
| JP | 2008534504 | 8/2008 |
| JP | 2009502788 | 1/2009 |
| RU | 2230748 | 6/2004 |
| WO | 9736912 | 10/1997 |
| WO | 9830574 A1 | 7/1998 |
| WO | 9856800 A1 | 12/1998 |
| WO | WO 99/21866 | 5/1999 |
| WO | 9928311 A1 | 6/1999 |
| WO | 0012521 A1 | 3/2000 |
| WO | 0031099 A1 | 6/2000 |
| WO | WO 00/44761 | 8/2000 |
| WO | WO 00/62783 | 10/2000 |
| WO | 0110878 A1 | 2/2001 |
| WO | WO 02/50092 | 6/2002 |
| WO | 03004509 A2 | 1/2003 |
| WO | 2003004509 | 1/2003 |
| WO | 03072141 A1 | 9/2003 |
| WO | 2004080391 A2 | 9/2004 |
| WO | 2004101587 | 11/2004 |
| WO | 2005074945 | 8/2005 |
| WO | 2005108412 | 11/2005 |
| WO | WO 2005/105821 | 11/2005 |
| WO | 2006050941 | 5/2006 |
| WO | 2006050942 | 5/2006 |
| WO | 2006087642 | 8/2006 |
| WO | 2007008537 | 1/2007 |
| WO | 2007059307 A2 | 5/2007 |
| WO | 2007060627 | 5/2007 |
| WO | 2007143507 | 12/2007 |
| WO | 2009055557 | 4/2009 |
| WO | 2010048599 | 4/2010 |
| WO | 2010048600 | 4/2010 |
| WO | 2010048601 | 4/2010 |
| WO | 2011008193 | 1/2011 |
| WO | 2011112864 A1 | 9/2011 |
| WO | 2011119604 | 9/2011 |
| WO | 2011146829 | 11/2011 |
| WO | 2013148891 | 10/2013 |
| WO | 2014145210 | 9/2014 |
| WO | 2014152326 | 9/2014 |

OTHER PUBLICATIONS

Vince, R., et al. Antimicrobial Agents and Chemotherapy, vol. 8, No. 4, 1975, 439-443.

Or et al., "Design, Synthesis, and Antimicrobial Activity of 6-0-Substituted Ketolides Active Against Resistant Respiratory Tract Pathogens", *J. Med. Chem.*, 43:1045-49 (2000).

Champney et al., "Structure-Activity Relationships for Six Ketolide Antibiotics", *Current Microbiology*, 42:203-10 (2001).

Denis et al., "β-Keto-Ester Chemistry and Ketolides. Snythesis and antibacterial Activity of 2-Halogeno, 2-Methyl and 2,3 Enol-Ether Ketolides", *Bioorganic & Medicinal Chemistry Letters*, 10:2019-22 (2000).

Tornøe et al. "Peptidotriazoles on Solid Phase: [1,2,3]-Triazoles by Regiospecific Copper(I)-Catalyzed 1,3-Dipolar Cycloadditions of Terminal Alkynes to Azides", *J. Org. Chem.*, 67:3057-64 (2002).

Rostovtsev, V.V. et al., "A Stepwise Huisgen Cycloaddition Process: Copper(I)=Catalyzed Regioselective "Ligation" of Azides and Terminal Alkynes," Angew. Chem. Int. Ed., 41: 2596-2599 (2002).

Baker, W.R. et al., "Modification of macrolide antibiotics. Synthesis of 11-deoxy-11-(carboxyamino)-6-O-methylerythromycin A 11,12-(cyclic esters) via an intramolecular Michael reaction of O-carbamates with an alpha , beta -unsaturated ketone," J. Org. Chem., 53:2340-2345, 1988.

Djokic, S. et al., "Erythromycin Series. Part 11. Ring Expansion of Erythromycin A Oxime by the Beckmann Rearrangement."J. Chem. Soc,, Perkin Trans 1., 1881-1890 (1986).

Phan, L.T. et al., "Synthesis of 2-Fluoro-6-O-propargyl-11,12-carbamate Ketolides. A Novel Class of Antibiotics," Org. Ltrs., 2:2951-2954 (2000).

Liang et al., "Synthesis and biological activity of new 5-O-sugar modified ketolide and 2-fluoro-ketolide antibiotics," Bioorg. Med. Chem. Lett., vol. 15, 2005, pp. 1307-1310.

Plata et al., "The synthesis of ketolide antibiotic ABT-773 (cethromycin)," Tetrahedron, vol. 60, 2004, pp. 10171-10180.

Ma et al., Curr. Med. Chem., "Anti-Infective Agents," vol. 1, 2002, pp. 15-34.

Barcia-Macay, Maritza, et al., 'Pharmacodynamic Evaluation of the Intracellular Activities of Antibiotics Against Staphylococcus

(56) References Cited

OTHER PUBLICATIONS

Aureus in a Model of THP-1 Macrophages', 2006, Antimicrobial Agents and Chemotherapy. vol. 50, No. 3, pp: 841-851.

Bebear, C.M., et al., in vitro activity of trovafloxacin compared to those of five antimicrobials against mycoplasmas including Mycoplasma hominis and Ureaplasma urealyticum fluoroquinolone-resistant isolates that have been genetically characterized, Antimicrob Agents Chemother 44:2557-2560 (2000).

Duffy, L., et al., Fluoroquinolone resistance in Ureaplasma parvum in the United States, J Clin Microbiol 44:1590-1591 (2006).

Waites, K.B., et al., Mycoplasmas and ureaplasmas as neonatal pathogens, Clin Microbiol Rev 18:757-89 (2005).

Holzer, G., et al., "Ka1,2 and KB1,3 X-Ray Emission Lines of the 3d Transition Metals", Dec. 1997, Physical Review, vol. 56, No. 6, pp: 4554-4568.

Berge, Stephen M., et al., "Pharmaceutical Salts", 1977, Journal of Pharmaceutical Sciences, vol. 66, No. 1, pp. 1-19.

Bermudez, Luiz E., et al., "Telithromycin is Active Against Mycobacterium Avium in Mice Despite Lacking Significant Activity in Standard In Vitro and Macrophage Assays and Is Associated with Low Frequency of Resistance During Treatment", 2001, Antimicrobal Agents and Chemotherapy, vol. 45, No. 8, pp. 2210-2214.

Bermudez, Luiz E., et al., "EDP-420, a Bicyclolide (Bridged Bicyclic Macrolide), Is Active Against Mcyobacterium Avium", 2007, Antimicrobal Agents and Chemotherapy, vol. 51, No. 5, pp. 1666-1670.

Cynamon, M. H., et al., "Activity of ABT-773 Against Mycobacterium Avium Complex in the Beige Mouse Model", 2000, Antimicrobal Agents and Chemotherapy, vol. 44, No. 10, pp. 2895-2896.

Patel, Ramesh N., "Stereoselective Biocatalysis", 2000, Bristol-Myers Squibb Research Institute; pp. 775-797.

Vennerstrom, Jonathan L., et al., "Identification of an Antimalarial Synthetic Trioxolane Drug Development Candidate", 2004, Letters to Nature, vol. 430, pp. 900-904.

Zuckerman, "Macrolides and ketolides: azithromycin, clarithromycin, telithromycin", Infectious Disease Clinics of North America, vol. 18, (2004), pp. 621-649.

Crone, Julia, et al., "Evaluation of a monoclonal antibody-based test for detection of Helicobacter pylori-Specific Antigen in stool samples from mice," Jul. 2004, Clinical and Diagnostic Laboratory Immunology, vol. 11, No. 4, pp. 799, 800.

Laine, Loren, et al., "Prospective comparison of H&E, Giemsa and Genta stains for the diagnosis of Helicobacter pylori," 1997, Gastrointestinal Endoscopy, vol. 45, No. 6, pp. 463-467.

Lee, Adrian et al., "A standard mouse model of Helicobacter pylori infection: introducing the Sydney Strain," 1997, Gastroenterology, vol. 112, pp. 1386-1397.

Drusano, G. L., et al."Is 60 Days of Ciprofloxacin Adminstration Necessary for Postexposure Prophylaxis for Bacillus Anthracis?", 2008, Antimicrobial Agents and Chemotherapy. vol. 52, No. 11, pp. 3973-3979.

Feder, P. I., et al., 1991. Statistical Analysis of Dose-Response Experiments by Maximum Likelihood Analysis and Iteratively Reweighted Nonlinear Least Squares Regression Techniques, 1991, Drug Information Journal, vol. 28, pp. 323-334.

Inglesby, Thomas V., et al., "Anthrax as a Biological Weapon, 2002", 2002, Journal of the American Medical Association, vol. 287, No. 17, pp. 2236-2252.

Celebuski, J.E. et al., 'Chemical Modification of Erythromycin: Novel Reaction Observed by Treatment with Metalloporphyrins', vol. 35, No. 23, pp. 3837-3850, 1994, Elsevier Science Ltd.

Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.

Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.

Physicians' Desk Reference, p. 2905, (2007).

Nilius et al.: 'Ketolides: the future of the macrolides?' Current Opinion in Pharmacology, [Online] vol. 2, Jan. 14, 2002, pp. 1-8 Retrieved from the Internet: <URL:http://www.sciencedirect.com/science/article/pii/S1471489202001984>.

Caira MR, "Crystalline polymorphism of orgainic compounds," Design of Organic Solids, Topics in Current Chemistry, Springer Berlin Heidelberg, 1998, p. 163-208.

Pathak et al., "Enzymatic Protecting Group Techniques in Organic Synthesis," Stereosel, Biocatal., 2000; pp. 775-797.

Jones et al.: 'MIC Quality Control Guidelines and Disk Diffusion Test Optimization for CEM-101, a Novel Fluoroketolide' Journal of Clinical Microbiology vol. 48, No. 4, Dec. 30, 2009, pp. 1470-1473.

Katz, Leonard, and Gary W. Ashley. "Translation and protein synthesis: macrolides." Chemical reviews 105.2 (2005): 499-528.

Threlfall, Terence L. "Analysis of organic polymorphs. A review." Analyst 120.10 (1995): 2435-2460.

Petit, Samuel, and Gerard Coquerel. "The amorphous state." Polymorphism: In the Pharmaceutical Industry 10 (2006): 1.

Organic Compounds Crystal Manufacture Handbook—Principles and Knowhow, 2008, pp. 57 to 84.

Hancock, Bruno C., Sheri L. Shamblin, and George Zografi. "Molecular mobility of amorphous pharmaceutical solids below their glass transition temperatures." Pharmaceutical research 12.6 (1995): 799-806.

Ashizawa, Kazuhide, "Physico-Chemical Studies on the molecular Details of Drug Crystals," Phar Tech Japan, 2002, vol. 18, No. 10. pp. 81-96.

PCT Search Report and Written Opinion prepared for PCT/US2009/061978 mailed Dec. 9, 2009.

Jensen, J.S., et al., Azithromycin Treatment Failure in Mycoplasma genitaliumPositive Patients with Nongonococcal Urethritis Is Associated with Induced Macrolide Resistance, Clin Infect Dis 47:1546-53 (2008).

Lemaire, Sandrine, et al., "Cellular Accumulation and Pharmacodynamic Evaluation of the Intracellular Activity of CEM-101, a Novel Fluoroketolide, Against Staphylococcus Aureus, Listeria Monocytogenes and Legionella Pneumophila in Human THP-1 Macrophages", 2009, Antimicrobial Agents and Chemotherapy. vol. 53, No. 9, pp. 3734-3743.

Li, X., et al., Emerging macrolide resistance in Mycoplasma pneumoniae in children: detection and characterization of resistant isolates, Pediatr Infect Dis J, 28:693-696 (2009).

European Search Report for EP 09 82 2827, dated Mar. 21, 2012.

International Search Report for PCT/US2009/061977, dated Dec. 23, 2009, (3 pages).

PCT International Search Report and Written Opinion for PCT/US2011/029424, mailed May 25, 2011.

PCT Search Report/Written Opinion prepared for PCT/US2010/048540, mailed Oct. 21, 2010.

PCT Search Report and Written Opinion for PCT/US2011/037330 completed Aug. 26, 2011.

Byrn, S., Pfeiffer, R., Ganey, M., Hoiberg, C., & Poochikian, G. (1995). Pharmaceutical solids: a strategic approach to regulatory considerations. Pharmaceutical research, 12(7), 945-954.

Sumerkan, B., Aygen, B., Doganay, M., & Sehmen, E. (1996). Antimicrobial susceptibility of Bacillus anthracis against macrolides. Salisbury Med Bull Supplement, 87, 138.

Maurin, M., Mersali, N. F., & Raoult, D. (2000). Bactericidal activities of antibiotics against intracellular Francisella tularensis. Antimicrobial agents and chemotherapy, 44(12), 3428-3431.

Luna, V. A., King, D. S., Gulledge, J., Cannons, A. C., Amuso, P. T., & Cattani, J. (2007). Susceptibility of Bacillus anthracis, Bacillus cereus, Bacillus mycoides, Bacillus pseudomycoides and Bacillus thuringiensis to 24 antimicrobials using Sensititre® automated microbroth dilution and Etest® agar gradient diffusion methods. Journal of antimicrobial chemotherapy, 60(3), 555-567.

(56) References Cited

OTHER PUBLICATIONS

Barthel, D., Schlitzer, M., & Pradel, G. (2008). Telithromycin and quinupristin-dalfopristin induce delayed death in Plasmodium falciparum. Antimicrobial agents and chemotherapy, 52(2), 774-777.
Still, J. G., et al. "Single Oral Dose Pharmacokinetics and Safety of CEM-101 in Healthy Subjects." 46th Annual Meeting. Idsa, 2008.
Lee, Joo Hyun, and Myung Gull Lee. "Dose-dependent pharmacokinetics of telithromycin after intravenous and oral administration to rats: contribution of intestinal first-pass effect to low bioavailability." J. Pharm. Pharm. Sci 10 (2007): 37-50.
Chen, M., Muri, E. M., Jacob, T. M., & Williamson, J. S. (2003). Synthesis and bioactivity of erythromycin derivatives. Medicinal chemistry research, 12(3), 111-129.
Kerdesky, F. A., Premchandran, R., Wayne, G. S., Chang, S. J., Pease, J. P., Bhagavatula, L., . . . & King, S. A. (2002). Synthesis of 2'-0-Benzoyl-3-keto-6-O-propargyl-11, 12-carbamoyl Erythromycin A. Organic process research & development, 6(6), 869-875.
Zhu, Z. J., Krasnykh, O., Pan, D., Petukhova, V., Yu, G., Liu, Y., . . . & Franzblau, S. G. (2008). Structure-activity relationships of macrolides against Mycobacterium tuberculosis. Tuberculosis, 88, S49-S63.
Putnam S. D. et al, Antimicrobial Characterization Of Solithromycin (Cem-101), A Novel Fluroroketolide: Activity Against Staphlococci and Enterococci. International Journal of Antimicrobial Agents, vol. 37, No. 1, 2011, pp. 39-45.
Written Opinion, Singapore Application No. 11201405895U: Intellectual Property Office of Singapore; Mar. 31, 2015, 6 pages.
Database WPI Week 200822 Thomson Scientific, London, GB; AN 2008-D02982.
Zimmermann, Torsten, et al. "Comparative tolerability of intravenous azithromycin, clarithromycin and erythromycin in healthy volunteers." Clinical Drug Investigation 21.8 (2001): 527-536.
Luke, D. R., and G. Foulds. "Toleration of intravenous azithromycin." The Annals of pharmacotherapy 31.9 (1997): abstract only.
Cannon, John B., N. Adeyinka Williams, and Karen J. Papp. "Reduction of pain on intravenous infusion with bile salt formulations for a macrolide antibiotic." International journal of pharmaceutics 114.1 (1995): abstract only.
Lu, Yan, YanJiao Wang, and Xing Tang. "Formulation and thermal sterile stability of a less painful intravenous clarithromycin emulsion containing vitamin E." International journal of pharmaceutics 346.1 (2008): abstract only.
Llano-Sotelo, B., D. Klepacki, and A. S. Mankin. 2008. Binding and action of CEM-10, a new macrolide/ketolide in development for treating infections with macrolide-resistant and macrolide-susceptible bacteria. 48th Annu. Intersci. Conf. Antimicrob. Agents Chemother./46th Infect. Dis. Soc. Am. Ann. Meet., abstr. F1-3983.
International Search Report for PCT/US2015/015353, dated May 14, 2015, (8 pages).
Ferris, C. F., Lu, S. F., Messenger, T., Guillon, C. D., Heindel, N., Miller, M., . . . & Simon, N. G. (2006). Orally active vasopressin V1a receptor antagonist, SRX251, selectively blocks aggressive behavior. Pharmacology Biochemistry and Behavior, 83(2), 169-174.
Amsden, G. W. "Anti-inflammatory effects of macrolides" an underappreciated benefit in the treatment of community-acquired respiratory tract infections and chronic inflammatory pulmonary conditions?. Journal of Antimicrobial Chemotherapy 55.1 (2005): 10-21.
de Jong, J. T., et al. "[Large-scale, acute, bacterial gastroenteritis caused by the enterotoxin of Staphylococcus aureus after a barbecue]." Nederlands tijdschrift voor geneeskunde 148.43 (2004): 2136-2140.
Raj, Pushker. "Pathogenesis and laboratory diagnosis of *Escherichia coli*" associated enteritis. Clinical microbiology Newsletter 15.12 (1993): 89-93.
Ikeue, T., et al. "[Pneumonia caused by Nocardia nova]." Nihon Kokyuki Gakkai zasshi= the journal of the Japanese Respiratory Society 39.7 (2001): 492-497.
Thakkar, Shyam, and Radheshyam Agrawal. "A case of Staphylococcus aureus enterocolitis: a rare entity." Gastroenterology & hepatology 6.2 (2010): 115-117.
Wain, Harry, and Paul A. Blackstone. "Staphylococcal Gastroenteritis." The American journal of digestive diseases 1.10 (1956): 424.
Boyce, Thomas G., "Staphylococcal Food Poisoning," Merck Manuals (2015) 2 pages.
Lv Yang et al., "Polymorphic Drugs." Oct. 31, 2009, pp. 110-111.
Le Loir, Yves, Florence Baron, and Michel Gautier. "Staphylococcus aureus and food poisoning." Genet Mol Res 2.1 (2003): 63-76.
Brittain HG editor "Polymorphism in pharmaceutical solids", Chapter 1, p. 1-10 (Grant DJW) and Chapter 5, p. 183-226 (1999).
Graeme, A. O'May, Nigel Reynolds, and George T. Macfarlane. "Effect of pH on an in vitro model of gastric microbiota in enteral nutrition patients." Applied and environmental microbiology 71.8 (2005): 4777-4783.
Cotter, Paul D., and Colin Hill. "Surviving the acid test: responses of gram-positive bacteria to low pH." Microbiology and Molecular Biology Reviews 67.3 (2003): 429-453.
Lyczak, J. B., Cannon, C. L., & Pier, G. B. (2002). Lung infections associated with cystic fibrosis. Clinical microbiology reviews, 15(2), 194-222.
Wain, Harry, and Paul A. Blackstone. "Staphylococcal Gastroenteritis." The American journal of digestive diseases 1.10 (1956): 424-429.

\* cited by examiner

PROCESS FOR THE PREPARATION OF MACROLIDE ANTIBACTERIAL AGENTS

CROSS REFERENCE TO RELATED APPLICATIONS

This application is the U.S. national stage application under 35 U.S.C. §371 of International Application Serial No. PCT/US2008/080936 filed Oct. 23, 2008, which claims the benefit under 35 U.S.C. §119(e) of U.S. Provisional Application Ser. No. 60/982,446, filed Oct. 25, 2007, the disclosure of which is hereby incorporated herein by reference.

TECHNICAL FIELD

The invention described herein relates to processes for preparing macrolide antibacterial agents. In particular, the invention relates to intermediates and processes for preparing ketolides and other macrolides that include a 1,2,3-triazole substituted side chain.

BACKGROUND AND SUMMARY

The use of macrolides for various infectious diseases is well known. Erythromycin was the first compound of this class to be introduced into clinical practice. Since then, additional macrolides, including ketolides have garnered much attention for their ability to treat a wide range of disease states. In particular, macrolides are an important component of therapies for treating bacterial, protozoal, and viral infections. In addition, macrolides are often used in patients allergic to penicillins.

Illustrative of their wide ranging uses, macrolide compounds have been found to be effective for the treatment and prevention of infections caused by a broad spectrum of bacterial and protozoal infections. They are also useful for infections of respiratory tract and soft tissue infections. Macrolide antibiotics are found to be effective on beta-hemolytic streptococci, pneumococci, staphylococci and enterococci. They are also found to be effective against mycoplasma, mycobacteria, some rickettsia, and chlamydia.

Macrolide compounds are characterized by the presence of a large lactone ring, which is generally a 14, 15, or 16-membered macrocyclic lactone, to which one or more saccharides, including deoxy sugars such as cladinose and desosamine, may be attached. For example, erythromycin is a 14-membered macrolide that includes two sugar moieties. Spiramycin belongs to a second generation of macrolide compounds that include a 16-membered ring. Third generation macrolide compounds include for example semi-synthetic derivatives of erythromycin A, such as azithromycin and clarithromycin. Finally, ketolides represent a newer class of macrolide antibiotics that have received much attention recently due to their acid stability, and most importantly due to their excellent activity against organisms that are resistant to other macrolides. Like erythromycins, ketolides are 14-membered ring macrolide derivatives characterized by a keto group at the C-3 position (Curr. Med. Chem., "Anti-Infective Agents," 1:15-34 (2002)). Several ketolide compounds are currently under clinical investigation; however, telithromycin (U.S. Pat. No. 5,635,485) is the first compound in this family to be approved for use.

Liang et al. in U.S. Patent Appl. Pub. No. 2006/0100164, the disclosure of which is incorporated herein by reference, describes a new series of compounds, and an illustrative synthesis thereof. These new compounds show excellent activity against pathogenic organisms, including those that have already exhibited resistance to current therapies. In particular, Liang et al. describes compounds including those of formula (I):

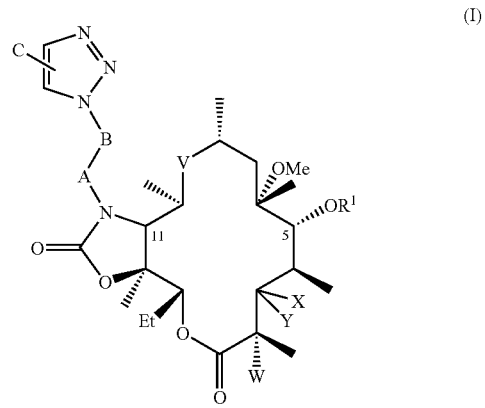

and pharmaceutically acceptable salts, solvates, and hydrates thereof; wherein $R^1$ is a monosaccharide or polysaccharide;

A is —CH$_2$—, —C(O)—, —C(O)O—, —C(O)NH—, —S(O)2-, —S(O)2NH—, —C(O)NHS(O)2-;

B is —(CH$_2$)$_n$— where n is an integer ranging from 0-10, or B is an unsaturated carbon chain of 2-10 carbons, which may contain any alkenyl or alkynyl group;

C represents 1 or 2 substituents independently selected in each instance from hydrogen, halogen, hydroxy, alkyl, aralkyl, alkylaryl, alkoxy, heteroalkyl, aryl, heteroaryl, heteroarylalkyl, aminoaryl, alkylaminoaryl, acyl, acyloxy, sulfonyl, ureyl, and carbamoyl, each of which is optionally substituted;

V is —C(O)—, —C(=NR$^{11}$)—, —CH(NR$^{12}$R$^{13}$)—, or —N(R$^{14}$)CH$_2$—; where R$^{11}$ is hydroxy or alkoxy, R$^{12}$ and R$^{13}$ are each independently selected from hydrogen, hydroxy, alkyl, aralkyl, alkylaryl, alkoxy, heteroalkyl, aryl, heteroaryl, heteroarylalkyl, dimethylaminoalkyl, acyl, sulfonyl, ureyl, and carbamoyl; and R$^{14}$ is hydrogen, hydroxy, alkyl, aralkyl, alkylaryl, alkoxy, heteroalkyl, aryl, heteroaryl, heteroarylalkyl, dimethylaminoalkyl, acyl, sulfonyl, ureyl, or carbamoyl;

W is hydrogen, F, Cl, Br, I, or OH; and

X is hydrogen; and Y is OR$^7$; where R$^7$ is hydrogen, a monosaccharide or disaccharide, including aminosugars or halosugars, alkyl, aryl, heteroaryl, acyl, such as 4-nitrophenylacetyl and 2-pyridylacetyl, or —C(O)NR$^8$R$^9$, where R$^8$ and R$^9$ are each independently selected from hydrogen, hydroxy, alkyl, aralkyl, alkylaryl, heteroalkyl, aryl, heteroaryl, heteroarylalkyl, alkoxy, dimethylaminoalkyl, acyl, sulfonyl, ureyl, and carbamoyl; or X and Y taken together with the attached carbon to form C=O.

In particular, the compound 11-N-[[4-(3-aminophenyl)-1,2,3-triazol-1-yl]-butyl]-5-desosaminyl-2-fluoro-3-oxoerythronolide A, 11,12-cyclic carbamate is described by Liang et al.

Due to the importance of these new compounds and others that are being used to provide beneficial therapies for the treatment of pathogenic organisms, alternative and/or improved processes for preparing these compounds are needed.

For example, the inventors hereof have discovered that side-reactions occur, and undesirable side-products and impurities are formed using the conventional synthesis of compounds of formula (I). Those side-reactions decrease the overall yield of the desired compounds, and those side-products and impurities may complicate the purification of the desired compounds. Described herein are new processes that may be advantageous in preparing compounds of formula (I) that avoid such side-products, and/or may be purified to higher levels of purity.

SUMMARY OF THE INVENTION

In one illustrative embodiment of the invention, processes for preparing compounds of formula (I) are described:

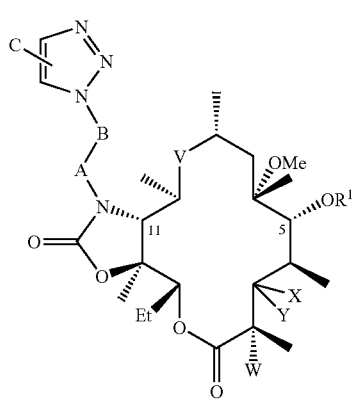

(I)

and pharmaceutically acceptable salts, solvates, and hydrates thereof; wherein $R^1$ is a monosaccharide or polysaccharide;

A is —CH$_2$—, —C(O)—, —C(O)O—, —C(O)NH—, —S(O)2-, —S(O)2NH—, —C(O)NHS(O)2-;

B is —(CH$_2$)$_n$— where n is an integer ranging from 0-10, or B is an unsaturated carbon chain of 2-10 carbons, which may contain any alkenyl or alkynyl group;

C represents 1 or 2 substituents independently selected in each instance from hydrogen, halogen, hydroxy, alkyl, aralkyl, alkylaryl, alkoxy, heteroalkyl, aryl, heteroaryl, heteroarylalkyl, aminoaryl, alkylaminoaryl, acyl, acyloxy, sulfonyl, ureyl, and carbamoyl, each of which is optionally substituted;

V is —C(O)—, —C(=NR$^{11}$)—, —CH(NR$^{12}$R$^{13}$)—, or —N(R$^{14}$)CH$_2$—; where R$^{11}$ is hydroxy or alkoxy, R$^{12}$ and R$^{13}$ are each independently selected from the group consisting of hydrogen, hydroxy, alkyl, aralkyl, alkylaryl, alkoxy, heteroalkyl, aryl, heteroaryl, heteroarylalkyl, dimethylaminoalkyl, acyl, sulfonyl, ureyl, and carbamoyl; R$^{14}$ is hydrogen, hydroxy, alkyl, aralkyl, alkylaryl, alkoxy, heteroalkyl, aryl, heteroaryl, heteroarylalkyl, dimethylaminoalkyl, acyl, sulfonyl, ureyl, or carbamoyl;

W is hydrogen, F, Cl, Br, I, or OH;

X is hydrogen; and Y is OR$^7$; where R$^7$ is hydrogen, a monosaccharide or disaccharide, including aminosugars or halosugars, alkyl, aryl, heteroaryl, acyl, such as 4-nitrophenylacetyl and 2-pyridylacetyl, or —C(O)NR$^8$R$^9$, where R$^8$ and R$^9$ are each independently selected from hydrogen, hydroxy, alkyl, aralkyl, alkylaryl, heteroalkyl, aryl, heteroaryl, heteroarylalkyl, alkoxy, dimethylaminoalkyl, acyl, sulfonyl, ureyl, and carbamoyl; or X and Y taken together with the attached carbon to form C=O.

In one aspect of the compounds of formula (I), V is C=O; X and Y are taken together with the attached carbon to form C=O. In another aspect, R$^1$ is a monosaccharide that includes an optionally protected 2'-hydroxy group. In another aspect, R$^1$ is a monosaccharide that includes a protected 2'-hydroxy group, where the protecting group is a sterically hindered acyl group, such as a branched alkyl, aryl, heteroaryl, arylalkyl, arylalkyl, or heteroarylalkyl acyl group, each of which is optionally substituted. In another aspect, -A-B— is alkylene, cycloalkylene, or arylene; and C is optionally substituted aryl or heteroaryl. In another aspect, R$^1$ is desosamine; -A-B— is 1,4-butylene and C is 4-(3-aminophenyl). In another aspect, W is F. In another aspect, R$^1$ is desosamine that includes a protected 2'-hydroxyl group, where the protecting group is a sterically hindered acyl group. In another aspect, the sterically hindered acyl group is benzoyl or substituted benzoyl.

In another illustrative embodiment, processes for preparing compounds of formula (II) are described:

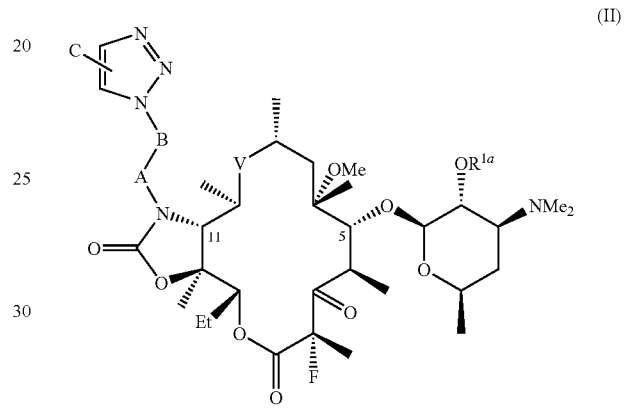

(II)

wherein R$^{1a}$ is a sterically hindered acyl group, and A, B, C, and V are as described herein. In one aspect of the compounds of formula (II), -A-B— is alkylene, cycloalkylene, or arylene; and C is optionally substituted aryl or heteroaryl. In another aspect, R$^{1a}$ is benzoyl; -A-B— is 1,4-butylene and C is 4-(3-aminophenyl).

In another illustrative embodiment, processes for preparing compounds of formula (III) are described:

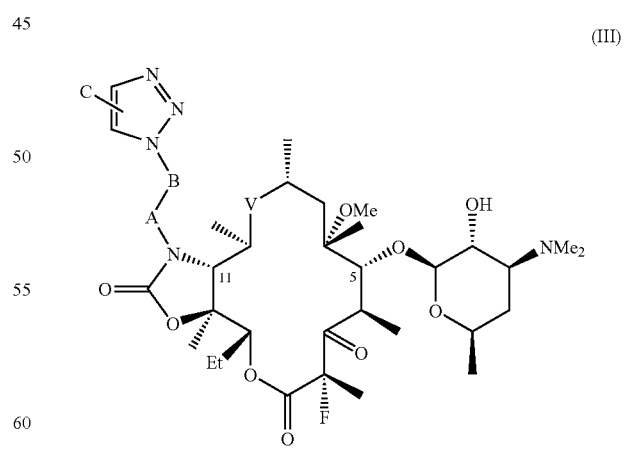

(III)

wherein A, B, C, and V are as described herein. In one aspect of the compounds of formula (III), -A-B— is alkylene, cycloalkylene, or arylene; and C is optionally substituted aryl or heteroaryl. In another aspect, -A-B— is 1,4-butylene and C is 4-(3-aminophenyl).

In another illustrative embodiment, a process is described for preparing a compound of formula (I), (II), or (III) comprising the step of (a) reacting a compound of formula (IV):

(IV)

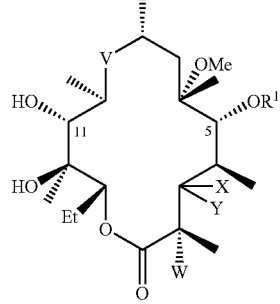

wherein $R^1$ is a monosaccharide that includes a 2'-hydroxyl group, and V, W, X, and Y are as defined herein, with a sterically hindered acylating agent $R^{1a}$-L, wherein $R^{1a}$ is a sterically hindered acyl group and L is a leaving or activating group, to form the corresponding 2'-acyl derivative. Illustratively, the process includes the step of (a) reacting compound (1) with a sterically hindered acylating agent to form the corresponding 2'-acyl or 2',4"-diacyl derivative, compound (2), as follows:

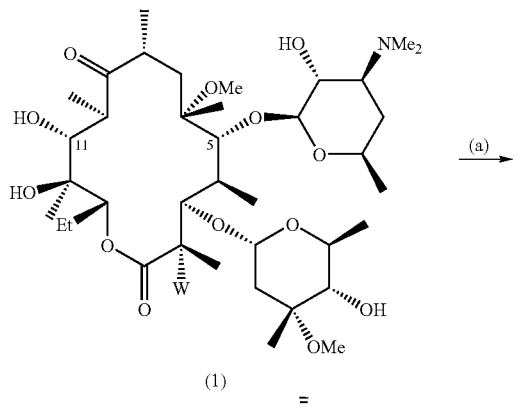

(1)

(a) →

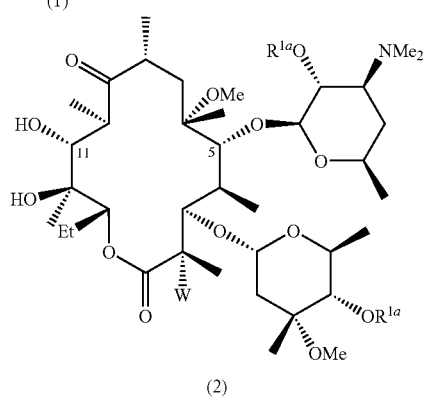

(2)

wherein W and $R^{1a}$ are as defined herein.

In another illustrative embodiment, a process is described for preparing a compound of formula (I), (II), or (III) comprising the step of (b) reacting a compound of formula (IV) with a carbonylating reagent to form a compound of formula (V):

(IV) →

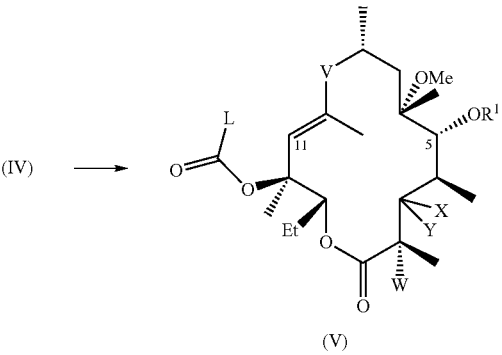

(V)

where L is a leaving group, and $R^1$, V, W, X, and Y are as defined herein. Illustratively, the process includes the step of (b) reacting compound (2) with carbonyldiimidazole to prepare compound (3):

(3)

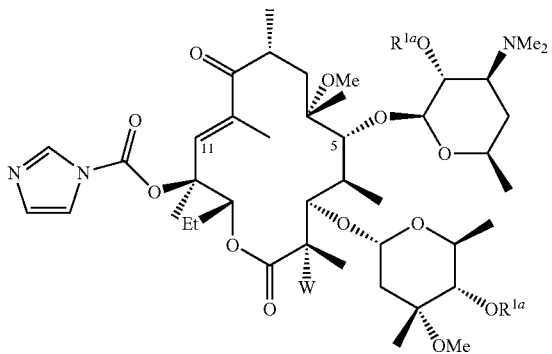

wherein $R^{1a}$ and W are as defined herein.

In another illustrative embodiment, a process is described for preparing a compound of formula (I), (II), or (III) comprising the step of (c) reacting a compound of formula (V) with a compound of formula $N_3$—B-A-$NH_2$ to obtain a compound of formula (VI):

(VI)

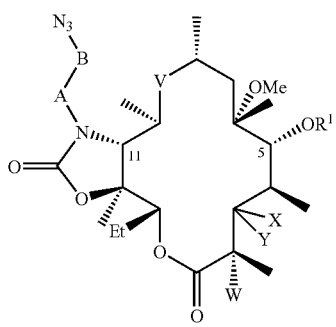

where $R^1$, A, B, V, W, X, and Y are as described herein. In one variation, A and B are taken together to form alkylene, cycloalkylene, including spirocycloalkylene, or arylene, each of which is optionally substituted. Illustratively, the process includes the step of (c) reacting compound (3) with $N_3$—B-A-$NH_2$ to obtain compound (4):

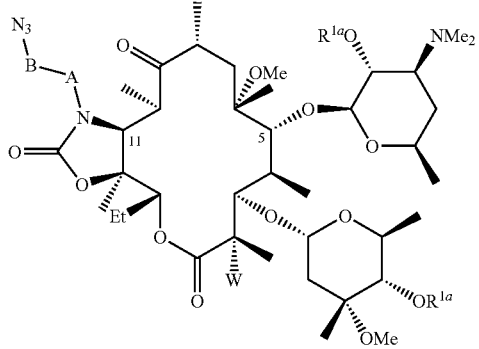

(4)

where $R^{1a}$, A, B, and W are as described herein.

In another illustrative embodiment, a process is described for preparing a compound of formula (I), (II), or (III) comprising the step of (d) reacting a compound of formula (I), where X is hydrogen and Y is $OR^7$; where $R^7$ is a monosaccharide or disaccharide with an acid to prepare the corresponding compound of formula (I) where $R^7$ is hydrogen. Illustratively, the process includes the step of (d) reacting compound (4) with an acid to prepare compound (5):

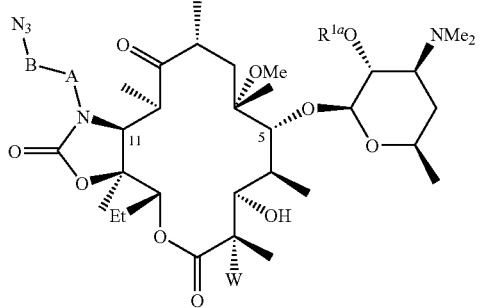

(5)

where $R^{1a}$, A, B, and W are as described herein.

In another illustrative embodiment, a process is described for preparing a compound of formula (I), (II), or (III) comprising the step of (e) oxidizing a compound of formula (I), where X is hydrogen and Y is OH, to prepare the corresponding compound of formula (I), where X and Y are taken together with the attached carbon to form C═O. Illustratively, the process includes the step of (e) oxidizing compound (5) with an oxidizing agent to prepare compound (6):

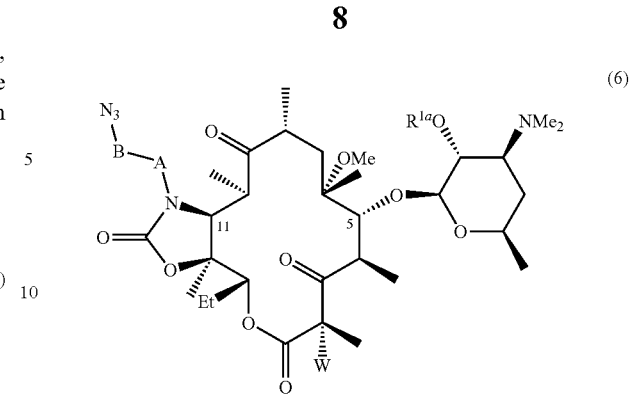

(6)

where $R^{1a}$, A, B, and W are as described herein.

In another illustrative embodiment, a process is described for preparing a compound of formula (I), (II), or (III) comprising the step of (f) reacting a compound of formula (I), where W is hydrogen, with a fluorinating agent to prepare the corresponding compound of formula (I) where W is F. Illustratively, the process includes the step of (f) reacting compound (6) with a fluorinating agent to prepare compound (7):

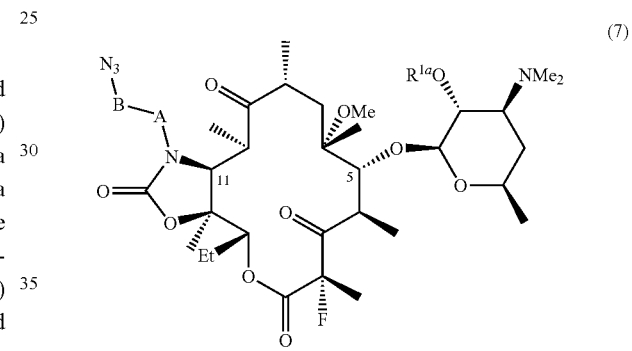

(7)

where $R^{1a}$, A, and B are as described herein.

In another illustrative embodiment, a process is described for preparing a compound of formula (I), (II), or (III) comprising the step of converting the azide group on a compound of formula (VI) into the corresponding compound of formula (I) having a 1,2,3-triazole group. Illustratively, a process is described for preparing a compound of formula (I), (II), or (III) comprising the step of (g) reacting a compound of formula (VI) with an $R^4,R^5$-substituted alkyne to obtain a compound of formula (VII):

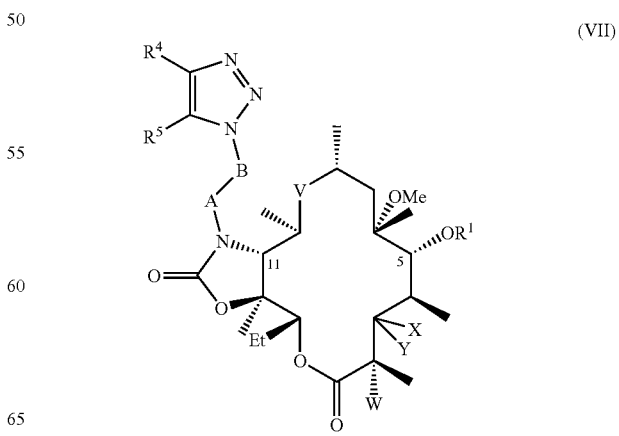

(VII)

where $R^4$ and $R^5$ are each independently selected from the group consisting of hydrogen, alkyl, heteroalkyl, aryl, and heteroaryl, each of which is optionally substituted, and $R^1$, A, B, V, W, X, and Y are as described herein. In one aspect, both $R^4$ and $R^5$ are not hydrogen. In another aspect, at least one of $R^4$ and $R^5$ is hydrogen. In one variation, A and B are taken together to form alkylene, cycloalkylene, including spirocycloalkylene, or arylene, each of which is optionally substituted. Illustratively, the process includes the step of (g) performing a Huisgen cyclization in the presence of a copper catalyst and base on compound (7) to prepare compound (8):

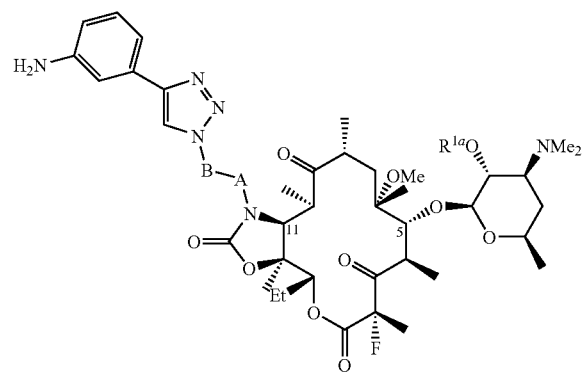

(8)

where $R^{1a}$, A, and B are as described herein.

In another illustrative embodiment, a process is described for preparing a compound of formula (I) comprising the step (h) of reacting a compound of formula (I), where $R^1$ is a monosaccharide or polysaccharide having a acyl protecting group, with an alcohol to prepare the corresponding deprotected compound of formula (I). In one variation, a process is described for preparing a compound of formula (III) comprising the step of reacting a compound of formula (II) with an alcohol. Illustratively, the process includes the step of (h) reacting compound (8) with an alcohol to prepare compound (9):

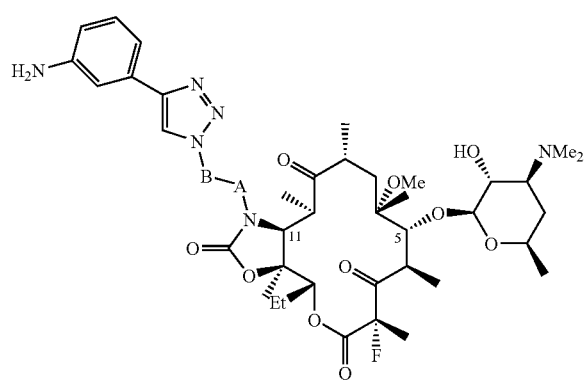

(9)

where A and B are as defined herein.

It is appreciated that the processes described herein may be advantageously performed simply and cost-effectively. It is further appreciated that the processes described herein may be scaled to large production batches. It is further appreciated that the processes described herein are performed in fewer steps than conventional processes. It is further appreciated that the processes described herein are performed in more convergent steps and fewer linear steps than conventional processes. It is further appreciated that the processes described herein may concomitantly produce fewer or different side products than known processes. It is further appreciated that the processes described herein may yield compounds described herein in higher purity than known processes.

DETAILED DESCRIPTION

In one illustrative embodiment, processes are described herein for preparing compounds of formulae (I), (II), and (III) wherein $R^1$ is a monosaccharide or polysaccharide. In one aspect, the monosaccharide is an aminosugar or a derivative thereof, such as a mycaminose derivatized at the C-4' position, desosamine, a 4-deoxy-3-amino-glucose derivatized at the C-6' position, chloramphenicol, clindamycin, and the like, or an analog or derivative of the foregoing. In another aspect, the polysaccharide is a disaccharide, such as a mycaminose derivatized at the C-4' position with another sugar or a 4-deoxy-3-amino-glucose derivatized at the C-6' position with another sugar, a trisaccharide, such as an aminosugar or halosugar, or an analog or derivative of the foregoing. In another embodiment, $R^1$ is desosamine, or an analog or derivative thereof. It is to be understood that in this and other embodiments, derivatives include protected forms of the monosaccharide or polysaccharide.

In another illustrative embodiment, a process is described for preparing a compound of formula (I), (II), or (III) comprising the step of (a) reacting a compound of formula (IV):

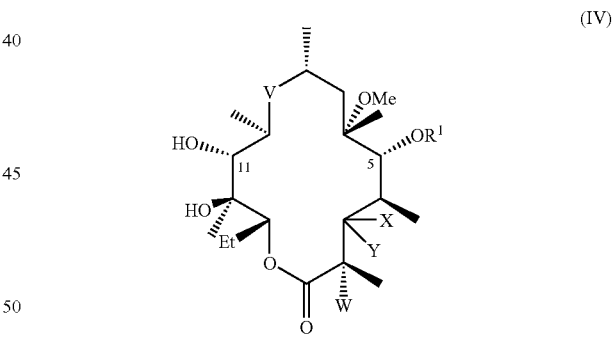

(IV)

wherein $R^1$ is a monosaccharide that includes a 2'-hydroxyl group, and V, W, X, and Y are as defined herein, with a sterically hindered acylating agent $R^{1a}$-L, wherein $R^{1a}$ is a sterically hindered acyl group and L is a leaving or activating group, to form the corresponding 2'-acyl derivative. It is appreciated that additional hydroxyl groups present on $R^1$ or that are included in the group Y may also be acylated in the process.

Illustrative sterically hindered acyl or diacyl derivatives include but are not limited to cyclohexylcarbonyl, benzoyl, pivaloyl, and the like. A wide variety of activating groups for forming the acyl derivative may be used to prepare the required acylating agent, including but not limited to anhydrides, chlorides, triflates, bromides, and the like. In one aspect, the sterically hindered acylating agent is benzoic anhydride, or an equivalent activated benzoyl reagent capable of forming a benzoyl ester at the 2' or both the 2' and 4' positions of a compound of formula (IV), or alternatively compound (1). Illustratively, the process includes the step of (a) reacting compound (1) with a sterically hindered acylating agent to form the corresponding 2'-acyl or 2',4''-diacyl derivative, compound (2), as follows:

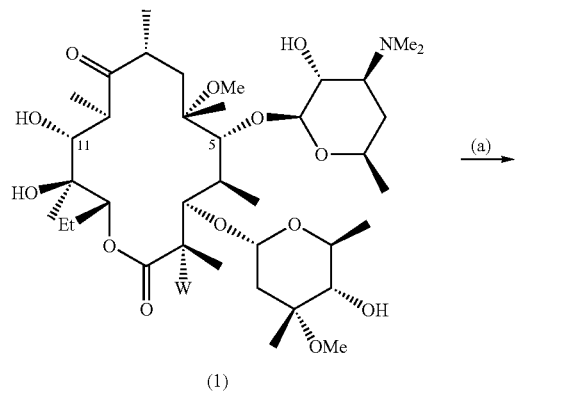

(1)

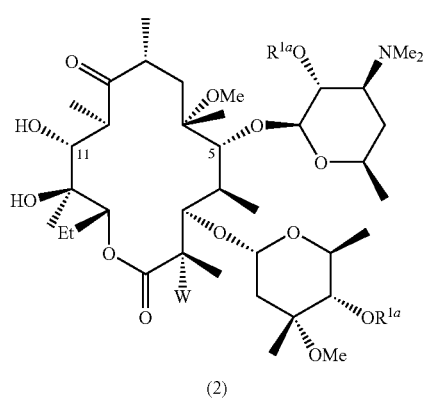

(2)

wherein W and $R^{1a}$ are as defined herein. In another aspect of the compounds of formulae (IV), (1), and (2), W is F. In one aspect of the conversion of (1) to (2), $R^{1a}$ is an optionally substituted benzoyl group, and step (a) includes benzoic anhydride, or an equivalent activated benzoylating reagent capable of forming the benzoyl ester at the 2' or both the 2' and 4' positions of a compound of formula (IV), or alternatively compound (1).

Step (a) is generally performed in the presence of a solvent and a base. Illustrative solvents include, but are not limited to, ethyl acetate, dichloromethane, acetone, pyridine and the like, and mixtures thereof. Illustrative bases include but are not limited to inorganic bases, such as sodium and potassium bicarbonates and carbonates, sodium and potassium hydroxides, and the like, and mixtures thereof; and amine bases, such as pyridine, dimethylaminopyridine (DMAP), triethylamine (TEA), diisopropylethylamine (DIPEA, Hünigs base), 1,4-diazabicyclo[2.2.2]octane (DABCO), and the like, and mixtures thereof. The reaction may be performed at a variety of temperatures, such as in the range from about 0° C. to about 60° C., and illustratively at about 10° C. to about 30° C.

In another illustrative embodiment, a process is described for preparing a compound of formula (I), (II), or (III) comprising the step of (b) reacting a compound of formula (IV) with a carbonylating reagent to form a compound of formula (V):

(IV) ⟶

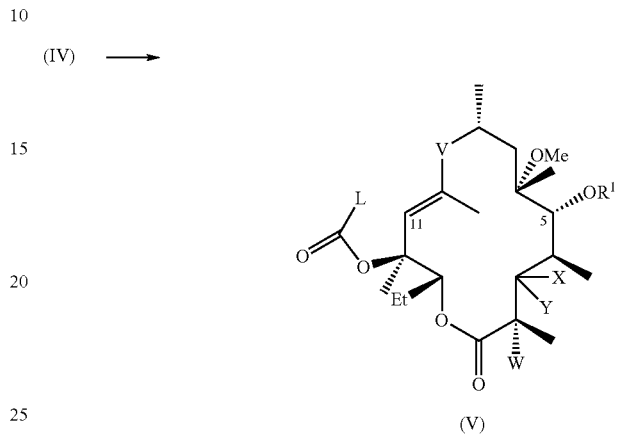

(V)

where L is a leaving group, and $R^1$, V, W, X, and Y are as defined herein. Step (b) is generally performed in presence of a polar solvent and a base to obtain a compound of formula (V). Illustrative carbonylating agents include methyl chloroformate, benzyl chloroformate and phenylchloroformate, carbonyldiimidazole, phosgene, diphosgene, triphosgene, 1,1'-carbonylbis(2-methylimidazole), [[1,1'-carbonyldipiperidine, bis(pentamethylene)urea]], dimethylcarbonate, diethylcarbonate, dipropylcarbonate, and the like. Illustrative polar solvents include, but are not limited to, dimethylformamide (DMF), acetonitrile, THF, methyl tetrahydrofuran, and the like, and mixtures thereof. Illustrative bases include, but are not limited to, DBU, DABCO, TEA, DIPEA, and the like, and mixtures thereof. The reaction may be performed at a variety of temperatures, such as in the range from about 0° C. to about 60° C., and illustratively at ambient temperature. Illustratively, the process includes the step of (b) reacting compound (2) with carbonyldiimidazole to prepare compound (3):

(3)

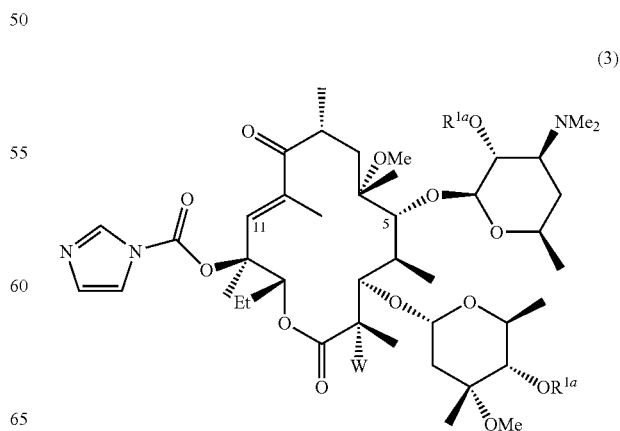

wherein $R^{1a}$ and W are as defined herein. In another illustrative example, the process includes the step of reacting compound (2) with carbonyldiimidazole in the presence of DBU to prepare compound (3). In another aspect of the compounds of formulae (V) and (3), W is F. In one variation, compounds (1V) are first treated with $Ms_2O$/pyridine, then DBU/acetone, then NaH/CDI/DMF at −10° C. to prepare compounds (V).

In another illustrative embodiment, a process is described for preparing a compound of formula (I), (II), or (III) comprising the step of (c) reacting a compound of formula (V) with a compound of formula $N_3$—B-A-$NH_2$ to obtain a compound of formula (VI):

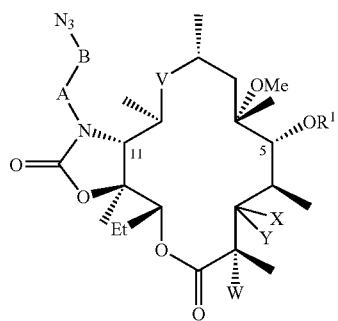

(VI)

where $R^1$, A, B, V, W, X, and Y are as described herein. In one variation, A and B are taken together to form alkylene, cycloalkylene, including spirocycloalkylene, or arylene, each of which is optionally substituted. Illustrative groups -A-B— include but are not limited to 1,4-butylene, 1,4-pentylene, 1,5-pentylene, 1,1-cyclopropylidene, 1,1-cyclopentylidene, 1-cycloprop-1-ylpropyl, and the like. In one aspect, -A-B— is linear $C_2$-$C_{10}$ alkylene. In another aspect, -A-B— is linear $C_3$-$C_5$ alkylene. In another aspect, -A-B— is 1,4-butylene.

Step (c) is generally performed in the presence of a polar solvent, including polar protic and polar aprotic solvents, or a mixture thereof. Illustrative polar protic solvents include, but are not limited to water, alcohols, such as methanol, ethanol, isopropanol, n-propanol, n-butanol, iso-butyl alcohol, tert-butyl alcohol, methoxyethanol, ethoxyethanol, pentanol, neo-pentyl alcohol, tert-pentyl alcohol, cyclohexanol, ethylene glycol, propylene glycol, benzyl alcohol, formamide, N-methylacetamide, N-methylformamide, glycerol, and the like, and mixtures thereof. Illustrative polar aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), acetonitrile, dimethylsulfoxide, propionitrile, ethyl formate, methyl acetate, hexachloroacetone, HMPA, HMPT, acetone, ethyl methyl ketone, ethyl acetate, isopropyl acetate, t-butyl acetate, sulfolane, N,N-dimethylpropionamide, nitromethane, nitrobenzene, tetrahydrofuran (THF), methyl tetrahydrofuran, dioxane, polyethers, and the like, and mixtures thereof. Additionally, step (c) can be performed in the presence of an additional base. Illustrative bases include, but are not limited to DBU, DABCO, TEA, DIPEA, and the like, and mixtures thereof.

Illustratively, the process includes the step of (c) reacting compound (3) with $N_3$—B-A-$NH_2$ to obtain compound (4)

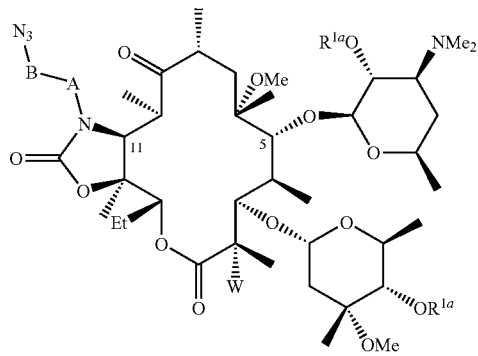

(4)

where $R^{1a}$, A, B, and W are as described herein. In one illustrative embodiment, the mole equivalent ratio of $N_3$—B-A-$NH_2$ to compound (3) is from about 4 to 1 to about 3 to 1. In another illustrative embodiment, the mole equivalent ratio of $N_3$—B-A-$NH_2$ to compound (3) is about 3 to 1. In another illustrative embodiment, the mole equivalent ratio of $N_3$—B-A-$NH_2$ to compound (3) is about 3 to 1 and the additional base is DBU in a mole equivalent ratio to compound (3) of from about 1 to 1 to about 0.75 to 1. In another illustrative embodiment, the mole equivalent ratio of $N_3$—B-A-$NH_2$ to compound (3) is about 3 to 1 and the additional base is DBU in a mole equivalent ratio to compound (3) of about 0.75 to 1.

In another illustrative embodiment, a process is described for preparing a compound of formula (I), (II), or (III) comprising the step of (d) reacting a compound of formula (I), where X is hydrogen and Y is $OR^7$; where $R^7$ is a monosaccharide or disaccharide with an acid to prepare the corresponding compound of formula (I) where $R^7$ is hydrogen. Illustrative acids include, but are not limited to, hydrochloric acid, hydrobromic acid, sulfuric acid, nitric acid, phosphoric acid, perchloric acid, trifluoroacetic acid, formic acid, hydrofluoric acid, and the like, and mixtures thereof. In one variation, the acid is hydrochloric acid. Step (d) is generally performed in a solvent such as water, a polar organic solvent, including alcohols such as methanol, ethanol, isopropanol, n-propanol, tert-butanol, n-butanol, and the like, and mixtures thereof. Step (d) may be performed at a wide variety of temperatures, including temperatures in the range from about 0° C. to about 70° C., and illustratively in the range from about 20° C. to about 60° C.

Illustratively, the process includes the step of (d) reacting compound (4) with an acid to prepare compound (5):

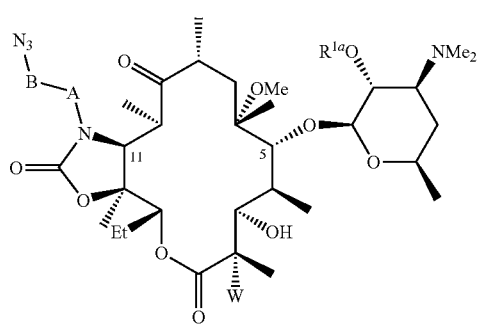

(5)

where $R^{1a}$, A, B, and W are as described herein. In one aspect of the compounds of formulae (VI), (4), and (5), W is F. Illustrative acids used in step (d) include, but are not limited to trifluoroacetic acid, formic acid, hydrochloric acid, hydrobromic acid, sulfuric acid, nitric acid, phosphoric acid, perchloric acid, hydrofluoric acid, and the like, and mixtures thereof.

In another illustrative embodiment, a process is described for preparing a compound of formula (I), (II), or (III) comprising the step of (e) oxidizing a compound of formula (I), where X is hydrogen and Y is OH, to prepare the corresponding compound of formula (I), where X and Y are taken together with the attached carbon to form C=O, Step (e) is generally performed using conventional oxidizing reagents and conditions, including but not limited to Corey-Kim oxidation, such as dimethylsulfide/N-chlorosuccinimide (DMS/NCS), di-n-butylsulfide/N-chlorosuccinimide, Dess-Martin reagent, Pfitzner-Moffat methods and modifications thereof, Swern conditions, such as DMSO/oxalyl chloride, DMSO/phosphorous pentoxide, DMSO/p-toluene sulfonyl chloride, DMSO/acetic anhydride, DMSO/trifluoroacetic anhydride, and DMSO/thionyl chloride, manganese, chromium and selenium reagents, tertiary amine oxides, Ni(Ac)$_2$/hypochlorite, DMSO/EDAC.HCl/pyridine.TFA and the like, and variations thereof, such as by including one or more phase-transfer catalysts.

Illustratively, the process includes the step of (e) oxidizing compound (5) with an oxidizing to prepare compound (6):

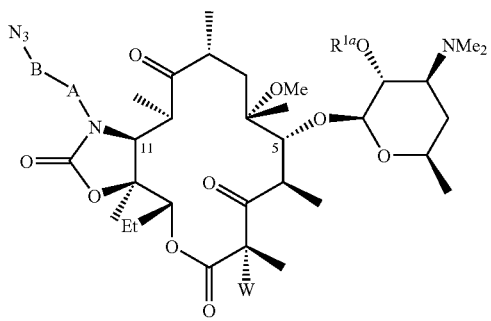

(6)

where $R^{1a}$, A, B, and W are as described herein. In one aspect of the compounds of formula (6), W is F. In one illustrative aspect, the oxidizing agent is selected from Swern conditions such as DMSO/EDAC.HCl/pyridine.TFA, Dess-Martin conditions, Corey-Kim conditions, such as dimethylsulfide/N-chlorosuccinimide, Jones reagent and other chromium oxidizing agents, permanganate and other manganese oxidizing agents, Ni(Ac)$_2$/hypochlorite, and others. The oxidation is illustratively carried out using dimethylsulfide, N-chlorosuccinimide and triethylamine in methylene chloride at a temperature of from about −20° C. to 0° C. In another illustrative embodiment, the oxidation is carried out using the Dess-Martin periodinane in methylene chloride at a temperature from about 5° C. to about 30° C. In another illustrative embodiment, the oxidation is carried out using the Dess-Martin periodinane in methylene chloride at a temperature from about 5° C. to about 30° C. utilizing a mole-equivalent ratio of Dess-Martin periodinane to compound (5) of from about 3.3 to 1 to about 1.3 to 1. In another illustrative embodiment, the oxidation is carried out using the Dess-Martin periodinane in methylene chloride at a temperature from about 5° C. to about 30° C. utilizing a mole-equivalent ratio of Dess-Martin periodinane to compound (5) of about 1.3 to 1.

In another illustrative embodiment, a process is described for preparing a compound of formula (I), (II), or (III) comprising the step of (f) reacting a compound of formula (I), where W is hydrogen, with a fluorinating agent to prepare the corresponding compound of formula (I) where W is F. Illustratively, the process includes the step of (f) reacting compound (6) with a fluorinating agent, such as (PhSO$_2$)$_2$N—F (NFSI or N-fluorosulfonimide), F-TEDA, F-TEDA-BF$_4$, 1-fluoro-4-hydroxy-1,4-diazoniabicyclo[2.2.2]octane bis(tetrafluoroborate), and the like, in the presence of solvent and base, such as t-BuOK, to prepare compound (7):

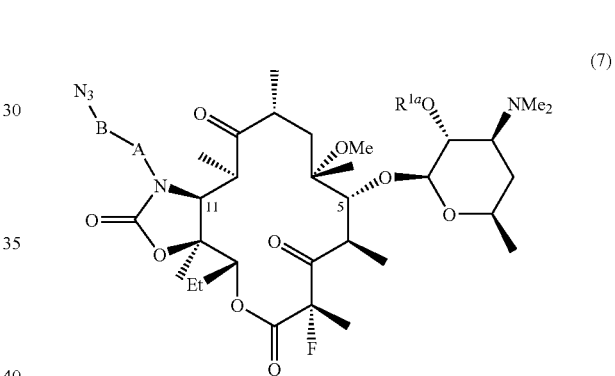

(7)

where $R^{1a}$, A, and B are as described herein. It is appreciated that other combinations of fluorinating agents and bases may be used to prepare compound (7). The fluorination reaction is generally performed in the presence of an inorganic base, such as sodium hydride, sodium or potassium carbonate, sodium or potassium bicarbonate and the like; an organic base, such as triethylamine, DABCO, potassium tert-butoxide, and the like; or a combination thereof. The fluorination reaction is generally performed in the presence of a solvent, including but not limited to, tetrahydrofuran, methyltetrahydrofuran, and the like, or mixtures thereof. In one illustrative embodiment, the fluorination agent is N-fluorosulfonimide, the base is potassium tert-butoxide, and the solvent is tetrahydrofuran. In another illustrative embodiment the mole equivalent ratio of N-fluorosulfonimide to compound (6) is from about 1.3 to 1 to about 1.2 to 1.

In another illustrative embodiment, a process is described for preparing a compound of formula (I), (II), or (III) comprising the step of converting the azide group on a compound of formula (VI) into the corresponding compound of formula (I) having a 1,2,3-triazole group. Illustratively, a process is described for preparing a compound of formula (I), (II), or (III) comprising the step of (g) reacting a compound of formula (VI) with an $R^4,R^5$-substituted alkyne to obtain a compound of formula (VII):

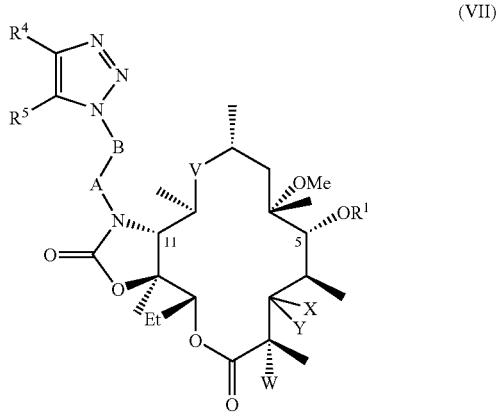

(VII)

where $R^4$ and $R^5$ are each independently selected from the group consisting of hydrogen, alkyl, heteroalkyl, aryl, and heteroaryl, each of which is optionally substituted, and $R^1$, A, B, V, W, X, and Y are as described herein. In one aspect, both $R^4$ and $R^5$ are not hydrogen. In another aspect, at least one of $R^4$ and $R^5$ is hydrogen. In another aspect of the compounds of formula (VII), W is F. In one variation, A and B are taken together to form alkylene, cycloalkylene, including spirocycloalkylene, or arylene, each of which is optionally substituted. Illustrative substituted alkynes include alkynes substituted with aromatic groups, substituted aromatic groups, heterocyclic groups, substituted heterocyclic groups, alkyl groups, branched alkyl groups, substituted alkyl groups, such as alkyl groups substituted with amino groups, including primary, secondary, and tertiary amino groups, one or more halogens, hydroxyls, ethers, including alkyl and aromatic ethers, ketones, thioethers, esters, carboxylic acids, cyanos, epoxides, and the like.

Illustratively, the process includes the step of (g) performing a Huisgen cyclization in the presence of a copper catalyst and base on compound (7) to prepare compound (8):

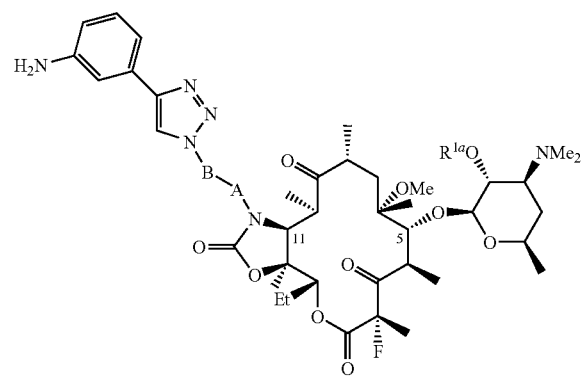

(8)

where $R^{1a}$, A, and B are as described herein. Huisgen cyclization in step (g) is carried out either solvent-free, in water or in an organic solvent such as acetonitrile or toluene, in the presence of base. Illustrative bases include but are not limited to organic bases, including alkyl and heteroaryl bases, such as triethylamine, diisopropylethylamine, DABCO, pyridine, lutidine, and the like, and inorganic bases, such as NaOH, KOH, $K_2CO_3$, $NaHCO_3$, and the like. The base is illustratively diisopropyl ethyl amine (DIPEA). In one embodiment the ratio of 3-aminophenylethyne to compound (7) is from about 1.5 to 1 to about 1.2 to 1 and the ratio of DIPEA to compound (7) is from about 10 to 1 to about 4 to 1. The reaction is carried out at temperatures ranging from 20° C. to 80° C. The reaction may also be promoted with the use of a catalyst, including but not limited to a copper halide, illustratively copper iodide. The ratio of CuI to azide (VI) or (7) is illustratively from about 0.01 to 1 to about 0.1 to 1. In one illustrative example, the ratio of CuI to azide (VI) or (7) is 0.03 to 1. In an alternate embodiment, the catalyst is an organic catalyst, such as phenolphthalein. Additional reaction conditions are described by Sharpless et al. in U.S. Patent Application Publication No. US 2005/0222427, Liang et al. in Bioorg. Med. Chem. Lett. 15 (2005) 1307-1310, and Romero et al. in Tetrahedron Letters 46 (2005) 1483-1487, the disclosures of which are incorporated herein by reference.

In another illustrative embodiment, a process is described for preparing a compound of formula (I) comprising the step (h) of reacting a compound of formula (I), where $R^1$ is a monosaccharide or polysaccharide having a acyl protecting group, with an alcohol to prepare the corresponding deprotected compound of formula (I). In one variation, a process is described for preparing a compound of formula (III) comprising the step of reacting a compound of formula (II) with an alcohol. Illustratively, the process includes the step of (h) reacting compound (8) with an alcohol to prepare compound (9):

(9)

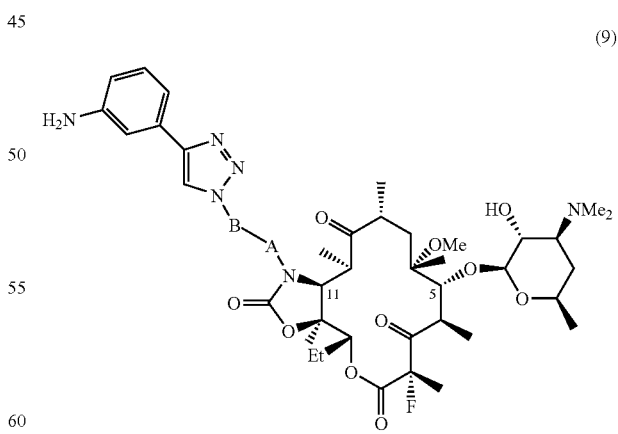

where A and B are as defined herein. The alcohol used in step (h) may be selected from methanol, ethanol, n-propanol, isopropanol, tert-butanol, n-butanol or mixtures thereof. Illustratively, the alcohol is methanol. The reaction is carried out at a temperature of about 0° C. to about 100° C. and preferably at about 20° C. to about 70° C. This reaction can also be carried out in presence of mineral acid selected from group comprising of HCl, H$_2$SO$_4$ and the like, and mixtures thereof. In one illustrative embodiment the reaction is carried out in methanol at a temperature of about 55° C.

It is to be understood that the steps described above for the various processes may generally be performed in a different order.

In another embodiment, processes are described herein for preparing compounds of formulae (I), (II), and (III), where the process includes the following steps:

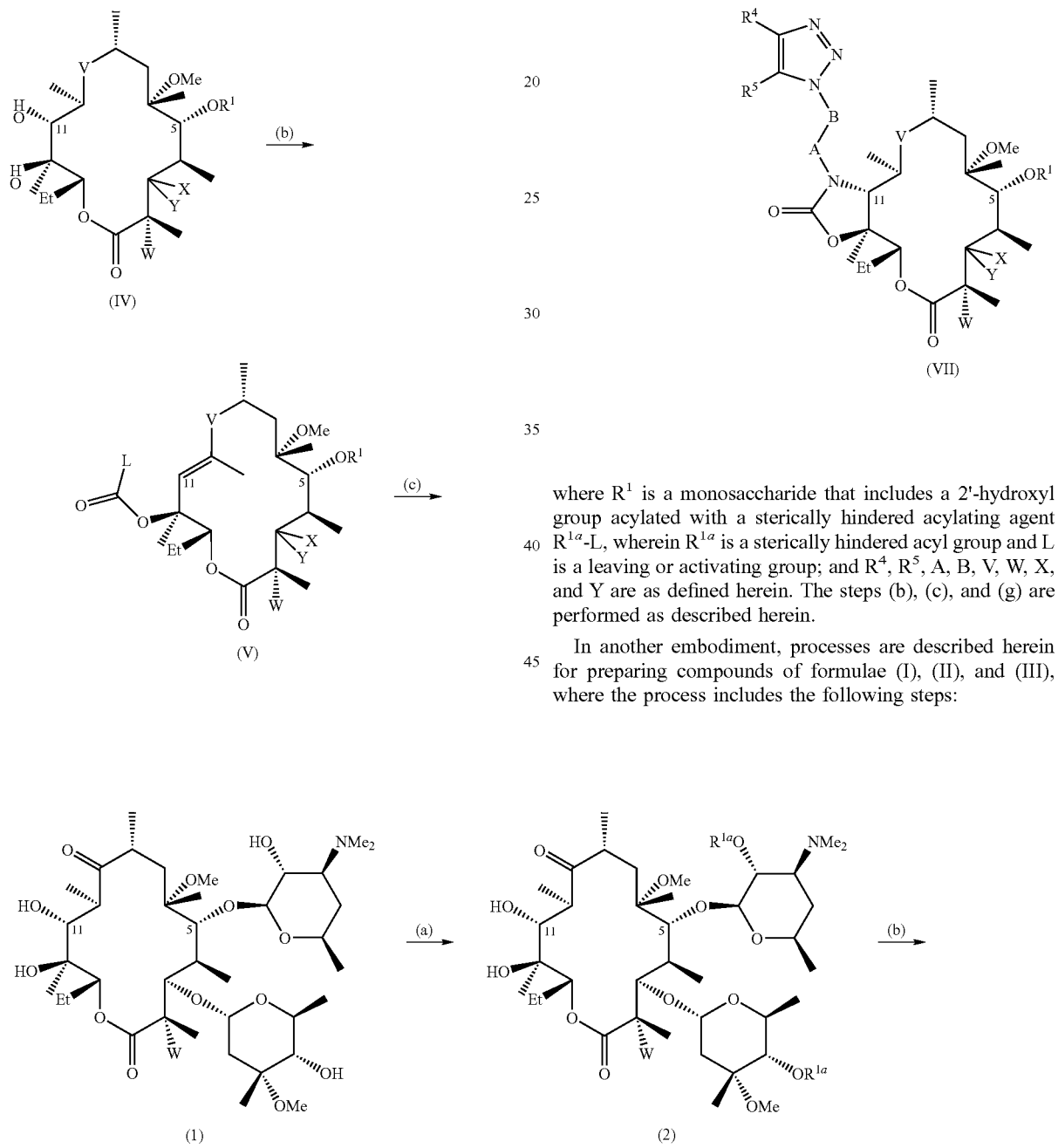

where R$^1$ is a monosaccharide that includes a 2'-hydroxyl group acylated with a sterically hindered acylating agent R$^{1a}$-L, wherein R$^{1a}$ is a sterically hindered acyl group and L is a leaving or activating group; and R$^4$, R$^5$, A, B, V, W, X, and Y are as defined herein. The steps (b), (c), and (g) are performed as described herein.

In another embodiment, processes are described herein for preparing compounds of formulae (I), (II), and (III), where the process includes the following steps:

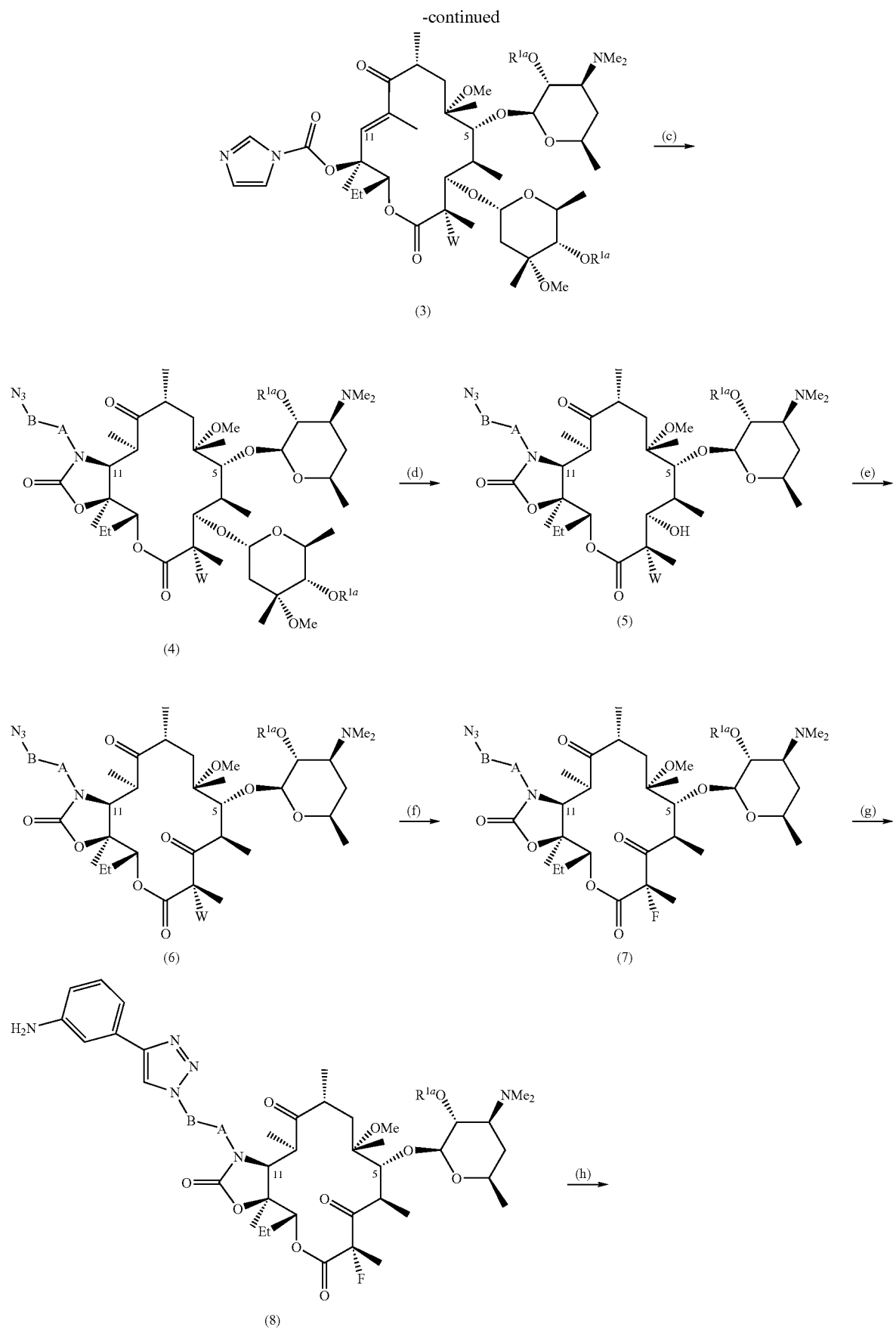

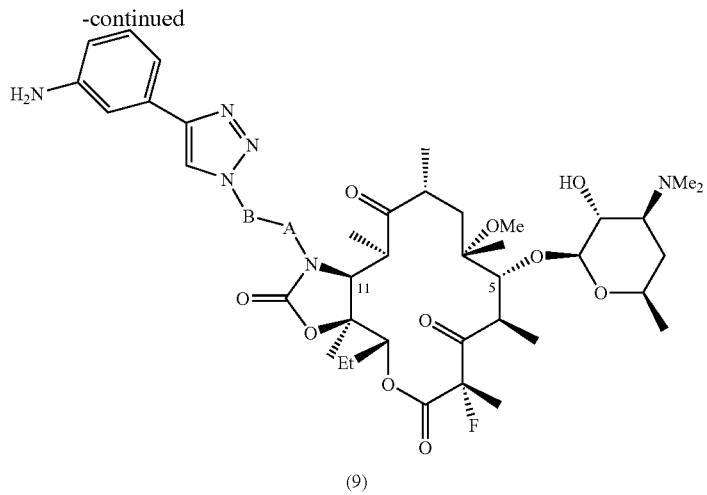

(9)

where $R^1$ is a monosaccharide that includes a 2'-hydroxyl group acylated with a sterically hindered acylating agent $R^{1a}$-L, wherein $R^{1a}$ is a sterically hindered acyl group and L is a leaving or activating group; and A, B, and W are as defined herein. The steps (a), (b), (c), (d), (e), (f), (g), and (h) are performed as described herein.

In another embodiment, intermediates useful for the preparation of compounds of formulae (I), (II), and (III) are described herein. Such intermediates include compounds of formula (IV), (V), (VI), and (VII), as well as compounds (1), (2), (3), (4), (5), (6), (7), (8), and (9). It is understood that such compounds are themselves useful in treating diseases, such as bacterial infections, and the like. It is also understood that such compounds may also be useful in the preparation of antibiotic, antibacterial, anti-infective, and/or antiviral compositions.

In another embodiment, the processes described herein are useful for preparing compounds of formulae (I), (II), and (III) in higher yields and/or purity than conventional processes. In one aspect, the processes described herein allow for the direct introduction of an azide side chain onto the macrolide without requiring the prior activation of a side chain hydroxyl group, such as by using tosyl chloride or an equivalent activating group, and subsequent conversion into the corresponding side chain azide group. The direct introduction of the azide side chain as described herein reduces the overall number of synthetic steps that must be performed in preparing compounds of formulae (I), (II), and (III). Conventional syntheses disclose the introduction of a side chain containing an alcohol group that must be converted into the azide in a linear sequence in at least two steps.

In another aspect, the processes described herein decrease the number of side product reactions that take place and correspondingly may decrease the number of undesired impurities found during the preparation of compounds of formulae (I), (II), and (III). The processes described herein include the use of a sterically hindered acyl group that functions both to protect a hydroxyl group on the saccharide moieties of the macrolide and also functions to decrease the likelihood of acyl migration from the saccharide to other functional groups on the compounds of formulae (I), (II), and (III). For example, it has been discovered that unhindered acyl groups, such as acetyl groups, present on the C-5 saccharide may migrate to other positions on the macrolide. In particular, it has been discovered that in the case of compounds (7), when $R^{1a}$ is acetyl, the acetyl protecting group migrates from desosamine to the aniline amino group of side chain, resulting in undesired product and subsequent additional purification steps. As described herein, the use of a sterically hindered acyl protecting group solves the problem of acyl migration reaction during the Huisgen cyclization. It is appreciated that avoiding the acyl migration may result in both an improved yield as well as improved purity. Accordingly, it has been discovered that compounds of formula (I), and in particular compounds (8) and (9) may be isolated by precipitation, filtration, centrifugation, decantation, and like processes without the need for chromatographic methods of purification. It is appreciated that compounds of formula (I), and in particular compound (9), can be further purified by solid-liquid adsorption chromatography. In one illustrative embodiment, the adsorbent solid is selected from a reverse-phase adsorbent, silica gel, alumina, magnesia-silica gel, or the like, and the elutant is selected from ethyl acetate, isopropyl acetate, methylene chloride, heptane, cyclohexane, toluene, acetonitrile, methanol, isopropanol, ethanol, THF, water or the like, or combinations thereof. In another illustrative example, the solid adsorbent is magnesia-silica gel.

In another aspect, the processes described herein improve the purity of the compounds of formulae (I), (II), and (III) described herein, and/or improve the purification of the compounds described herein. The processes described herein include the use of a sterically hindered acyl group that functions both to protect a hydroxyl group on the saccharide moieties of the macrolide and also functions to provide more effective purification of the compounds. For example, it has been discovered that performing the Huisgen cyclization leads to a mixture of triazole compound of formula (VII) and unreacted ethyne compound. When the triazole compound of formula (VII) includes a monosaccharide at $R^1$ that is not protected as described herein, the two compounds are difficult to separate. In contrast, when the triazole compound of formula (VII) does include a 2'-acyl-protected monosaccharide at $R^1$, the triazole compound of formula (VII) is unexpectedly more easily separated from the unreacted ethyne compound. Accordingly, it has been discovered that compounds of formula (VII), and in particular compounds (8) and (9) may be isolated by precipitation, filtration, centrifugation, decantation, and like processes without the need for chromatographic methods of purification. It is appreciated that compounds of formula (I), and in particular compounds (9), can be further purified by solid-liquid chromatography. In one illustrative embodiment, the adsorbent solid is selected from a reverse-phase adsorbent, silica gel, alumina, magnesia-silica gel, and the like, and the elutant is selected from ethyl acetate, isopropyl acetate, methylene chloride, heptane, cyclohexane, toluene, acetonitrile, methanol, isopropanol, ethanol, THF, water or the like, or combinations thereof. In another illustrative example, the solid adsorbent is magnesia-silica gel.

In another embodiment, compounds of formulae (I), (II), and (III) are described herein as having purities greater than about 98%, greater than about 99%, and greater than about 99.5%. In another embodiment, compounds of formulae (I), (II), and (III) are described herein as including less than about 1%, less than about 0.5%, less than about 0.2%, and less than about 0.1% of any aminophenylethyne compounds. In another embodiment, compounds of formulae (I), (II), and (III) are described herein as being substantially free or free of any aminophenylethyne compounds. In another embodiment, compositions including compounds of formulae (I), (II), and (III) are described herein as including less than about 1%, less than about 0.5%, less than about 0.15%, and less than about 0.1% of any aminophenylethyne compounds compared to the compounds of formulae (I), (II), and (III) in the composition. In another embodiment, compositions including compounds of formulae (I), (II), and (III) are described herein as being substantially free or free of any aminophenylethyne compounds.

The term "aryl," alone or in combination, refers to an optionally substituted aromatic ring system. The term aryl includes monocyclic aromatic rings and polyaromatic rings. Examples of aryl groups include but are not limited to phenyl, biphenyl, naphthyl and anthryl ring systems.

The term "heteroaryl" refers to optionally substituted aromatic ring systems having one or more heteroatoms such as, for example, oxygen, nitrogen, sulfur, selenium and phosphorus. The term heteroaryl may include five- or six-membered heterocyclic rings, polycyclic heteroaromatic ring systems and polyheteroaromatic ring systems.

As used herein the term aralkyl is equivalent to the term arylalkyl and denotes one or more unsubstituted or substituted monocyclic or unsubstituted or substituted polycyclic aromatic rings attached to an alkyl moiety; illustrative examples include but are not limited to benzyl, diphenylmethyl, trityl, 2-phenylethyl, 1-phenylethyl, 2-pyridylmethyl, 4,4'-dimethoxytrityl, and the like.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The term saccharide includes monosaccharides, disaccharides, and polysaccharides, each of which is optionally substituted. The term also includes sugars and deoxysugars optionally substituted with amino, amido, ureyl, halogen, nitrile, or azido groups. Illustrative examples include, glucosamine, N-acetylglucosamine, desosamine, forosamine, sialic acid, and the like.

The processes described herein are further illustrated by the following examples. The following examples are intended to be illustrative and should not be construed or considered to be limiting in any manner.

EXAMPLES

Example 1

Preparation of 2',4"-di-O-benzoyl-6-O-methylerythromycin A. 125 mL of ethyl acetate was added to 25 g clarithromycin A. 26.5 g benzoic anhydride, 5.7 g 4-dimethylamino pyridine and 6.7 g triethylamine were added to the reaction mixture at 25° C. to 35° C. The reaction mixture was stirred for about 70 hours at ambient temperature. After completion of the reaction, ethyl acetate was distilled out to obtain the title compound.

Example 2

Preparation of 10,11-anhydro-2',4"-di-O-benzoyl-12-O-imidazolylcarbonyl-6-O-methylerythromycin A. Dimethylformamide (DMF, 100 mL) was added to 2',4"-di-O-benzoyl-6-O-methylerythromycin A at 25-35° C., then 1,8-diazabicyclo[5.4.0]undec-7-ene (DBU 6.4 g) was added to the reaction mixture and stirred at ambient temperature. 1,1'-Carbonyldiimidazole (CDI, 17 g) was added to the reaction and it was stirred until completion at ambient temperature. The title compound is isolated by addition of water, and collecting the resulting precipitate.

Example 3

Preparation of 2',4"-di-O-benzoyl-11-N-(4-Azidobutyl)-6-O-methylerythromycin A 11,12-cyclic carbamate. DMF (50 mL) was added to 10,11-anhydro-2',4"-di-O-benzoyl-12-O-imidazolylcarbonyl-6-O-methylerythromycin A (10 g) at 25° C. to 35° C. 4-Azido butyl amine (4.4 g) and DBU (1.5 g) were added to the reaction mixture, which was stirred at 25° C. to 35° C. until the reaction was complete. The mixture was then treated with cold water, and the resulting solid precipitate was collected. The solid was treated with dichloromethane followed by extraction and removal of solvent to give the title compound. The mole-equivalent ratio of 4-azido butyl amine to 10,11-anhydro-2',4"-di-O-benzoyl-12-O-imidazolylcarbonyl-6-O-methylerythromycin A is optionally selected to be from about 4 to 1 to about 3 to 1. The molar ratio of DBU to 10,11-anhydro-2',4"-di-O-benzoyl-12-O-imidazolylcarbonyl-6-O-methylerythromycin A is optionally selected to be from about 1 to 1 to about 0.75 to 1.

Example 4

Preparation of 11-N-(4-Azidobutyl)-5-(2'-benzoyldesosaminyl)-3-hydroxy-6-O-methylerythronolide A 11,12-cyclic carbamate. Acetone (10 mL) was added to 2',4"-di-O-benzoyl-11-N-(4-Azidobutyl)-6-O-methylerythromycin A 11,12-cyclic carbamate (5 g) to obtain a clear solution at 25° C. to 35° C. Dilute HCl (10 mL) was added to the reaction mixture and it was stirred for 24 hours at ambient temperature. After the completion of the reaction, the reaction mixture was extracted with ethyl acetate and treated with a sodium hydroxide solution to give the title compound.

Example 5

Preparation of 11-N-(4-Azidobutyl)-5-(2'-benzoyldesosaminyl)-3-oxo-6-O-methylerythronolide A 11,12-cyclic carbamate. Dichloromethane (50 mL) was added to N-chlorosuccinimide (2 g) under nitrogen at room temperature cooled to 0° C. Dimethylsulfide (1.8 mL) was added slowly to the reaction mixture at 0° C. under stirring. 11-N-(4-Azidobutyl)-5-(2'-benzoyldesosaminyl)-3-hydroxy-6-O-methylerythronolide A 11,12-cyclic carbamate 11,12-cyclic carbamate (5 g) dissolved in dichloromethane (20 mL) was added drop wise to the reaction mixture at 0° C. under stirring. The mixture was cooled to about −20° C. and a solution of triethylamine (4 mL) in dichloromethane (5 mL) was added to the reaction mixture and stirred for 30 minutes. After completion of the reaction, it is treated with saturated sodium bicarbonate solution and the organic layer was isolated. The title compound was obtained by distillation of the solvent. Additional reaction conditions are described by Plata, et al, Tetrahedron 60 (2004), 10171-10180, the entire disclosure of which is incorporated herein by reference.

Example 5A

Preparation of 11-N-(4-Azidobutyl)-5-(2'-benzoyldesosaminyl)-3-oxo-6-O-methylerythronolide A 11,12-cyclic carbamate. Oxidation of 11-N-(4-azidobutyl)-5-(2'-benzoyldesosaminyl)-3-hydroxy-6-O-methylerythronolide A 11,12-cyclic carbamate (100 g, 0.1225 moles) with Dess-Martin periodinane (170 g, 0.400 moles) was carried out in dichloromethane at 10-15° C. Reaction mixture was stirred at 20-25° C. for 2 hr. The reaction mixture was quenched with 5% aqueous sodium hydroxide solution. The organic layer was washed with water and sat. solution of sodium chloride. The solvent was removed by distillation of the organic layer and the product was isolated from a mixture of diisopropyl ether and hexane. The separated solid was filtered and dried under vacuum at 30-35° C. to give the title compound. The mole-equivalent ratio of Dess-Martin periodinane to 11-N-(4-azidobutyl)-5-(2'-benzoyldesosaminyl)-3-hydroxy-6-O-methylerythronolide A 11,12-cyclic carbamate is optionally from about 3.3 to 1 to about 1.3 to 1.

Example 6

Preparation of 11-N-(4-Azidobutyl)-5-(2'-benzoyldesosaminyl)-3-oxo-2-fluoro-6-O-methylerythronolide A, 11,12-cyclic carbamate. To a solution of 11-N-(4-azidobutyl)-5-(2'-benzoyldesosaminyl)-3-oxo-6-O-methylerythronolide A 11,12-cyclic carbamate (5 g) in tetrahydrofuran (400 mL) was added 7.3 mL of potassium tert-butoxide followed by addition of 2 g of N-fluorobenzenesulfonimide. After about 1 hour, the mixture was quenched with water followed by extraction with dichloromethane. The organic layers were separated and concentrated to obtain the title compound.

Example 6B

Example 6

Preparation of 11-N-(4-Azidobutyl)-5-(2'-benzoyldesosaminyl)-3-oxo-2-fluoro-6-O-methylerythronolide A, 11,12-cyclic carbamate. To a solution of 11-N-(4-azidobutyl)-5-(2'-benzoyldesosaminyl)-3-oxo-6-O-methylerythronolide A 11,12-cyclic carbamate (100 g) in tetrahydrofuran (2200 mL) was added potassium tert-butoxide (28 g) at −20° C. to −5° C. followed by the addition of N-fluorobenzenesulfonimide (54 g). After about 1 hour, The mixture was quenched with 5% aqueous sodium bicarbonate solution. The separated organic layer was washed with water and saturated sodium chloride solution. The solvent was removed by distillation and remaining material was crystallized from the mixture of isopropyl alcohol and water, filtered, and dried under vacuum at 40-45° C. to yield the title compound. The mole-equivalent ratio of N-fluorobenzenesulfonimide to 11-N-(4-azidobutyl)-5-(2'-benzoyldesosaminyl)-3-oxo-6-O-methylerythronolide A 11,12-cyclic carbamate is optionally from about 1.6 to 1 to about 1.2 to 1. The ratio of solvent (mL) to 11-N-(4-azidobutyl)-5-(2'-benzoyldesosaminyl)-3-oxo-6-O-methylerythronolide A 11,12-cyclic carbamate is optionally from about 22 to 1 to about 17 to 1.

Example 7

11-N-(3-amino-phenyl-1-ylmethyl-[1,2,3]-triazole-1-yl]butyl)-5-(2'-benzoyldesosaminyl)-3-oxo-2-fluoro-erythronolide A, 11,12-cyclic carbamate. 11-N-(4-Azidobutyl)-5-(2'-benzoyldesosaminyl)-3-oxo-2-fluoro-6-O-methylerythronolide A, 11,12-cyclic carbamate (10 g), 3-ethynylphenylamine (2.11 g), copper iodide (0.3 g) and diisopropylethylamine (15.5 g) were taken in acetonitrile (200 mL) and stirred for 20 hours at room temperature. After completion of the reaction, the reaction mixture was quenched with dilute HCl and extracted with dichloromethane. The organic layer was neutralized with a bicarbonate solution, dried and concentrated to obtain the title compound.

Example 7B

11-N-(3-amino-phenyl-1-ylmethyl-[1,2,3]-triazole-1-yl]butyl)-5-desosaminyl-3-oxo-2-fluoro-erythronolide A, 11,12-cyclic carbamate. 11-N-(3-amino-phenyl-1-ylmethyl-[1,2,3]-triazole-1-yl]butyl)-5-(2'-benzoyldesosaminyl)-3-oxo-2-fluoro-6-O-methylerythronolide A, 11,12-cyclic carbamate (100 g), 3-ethynylphenylamine (20 g), copper iodide (10 g) and diisopropylethylamine (155 g) were taken in acetonitrile 600 mL) and stirred for 12 hours at 25° C. to 30° C. The mole equivalent ratio of 3-ethynylphenylamine to 11-N-(3-amino-phenyl-1-ylmethyl-[1,2,3]-triazole-1-yl]butyl)-5-(2'-benzoyldesosaminyl)-3-oxo-2-fluoro-6-O-methylerythronolide A, 11,12-cyclic carbamate is optionally from about 1.5 to 1 to about 1.2 to 1. After completion of the reaction, the reaction mixture was poured into dilute HCl and extracted with diisopropylether. The aqueous layer was extracted with dichloromethane. The dichloromethane layer was neutralized with aqueous sodium bicarbonate, dried (NaSO$_4$) and concentrated to obtain the title compound. This material was added to methanol (600 mL) and the resulting mixture heated at 50° C. to 55° C. for 12 hours. The solution was treated with activated carbon (10 g), filtered and concentrated under reduced pressure. The residue was dissolved in a mixture of water and EtOAc. The pH of the aqueous phase was adjusted to about 3.5. The organic layer was separated and the aqueous layer was extracted with ethyl acetate (two times) followed by diisopropylether (two times). The resulting aqueous layer was added to aqueous ammonia (1000 mL of about 4% ammonia). The precipitated solid was collected by filtration, washed with water, until the pH of the wash was about 7 to 8 and dried under reduced pressure to obtain the title compound. This material is optionally further purified by recrystallization from ethanol.

Example 8

11-N-(3-amino-phenyl-1-ylmethyl-[1,2,3]-triazole-1-yl]butyl)-5-desosaminyl-3-oxo-2-fluoro-erythronolide A, 11,12-cyclic carbamate. 11-N-(3-amino-phenyl-1-ylmethyl-[1,2,3]-triazole-1-yl]butyl)-5-(2'-benzoyldesosaminyl)-3-oxo-2-fluoro-erythronolide A, 11,12-cyclic carbamate (6 g) was dissolved in methanol (60 mL) and heated at reflux for 7 hours. After the completion of reaction, the mixture was concentrated, diluted with diisopropylether (30 mL) and stirred at ambient temperature for 2 hours. The resulting solid was collected by filtration. The solid is optionally purified by precipitation, crystallization or chromatography. Optionally, the material is converted to a salt by addition of an acid followed by precipitation of the salt. Analysis of the material indicated the title compound with >98% purity. Examples 1-8 were repeated to prepare a 5 kg sample of the title compound of Example 8. It was determined that the large sample contained less than about 0.1% aminophenylethynes, or about 0.07% aminophenylethynes.

Example 9

Purification of 11-N-(3-amino-phenyl-1-ylmethyl-[1,2,3]-triazole-1-yl]butyl)-5-desosaminyl-3-oxo-2-fluoro-erythronolide A, 11,12-cyclic carbamate. Florisil (21 kg) was loaded into a column containing 63 L of ethyl acetate. A solution of 1.4 kg of 11-N-(3-amino-phenyl-1-ylmethyl-[1,2,3]-triazole-1-yl]butyl)-5-desosaminyl-3-oxo-2-fluoro-erythronolide A, 11,12-cyclic carbamate in 14 L ethyl acetate and 0.7 L of acetonitrile is passed through the column. The eluent is collected. Ethyl acetate (112 L) is passed through the column and the eluent is combined with the first fraction. This process is repeated 4 additional times. The combined eluent solutions are concentrated and the residue was dissolved in 39 L of ethyl alcohol by heating to 50-55° C. The volume is reduce to about 22 L and cooled to 25-30° C. The solution is stirred for 5-6 hours. The resultant solid is collected and washed with cold ethyl alcohol. The wet cake is dissolved in a solution of ethyl acetate/acetonitrile (15 L/0.5 L per kg of wet cake) by heating to 40-45° C. Additional ethyl acetate (20 L per kg of wet cake) is added to the solution. This solution is passed through a Florisil column (15 kg/kg wet cake). The eluent is collected. The column is flushed with ethyl acetate (80 L per kg of wet cake). The eluent is collected and combine with the first eluent. The combined eluent solutions are concentrated and the residue was dissolved in 39 L of ethyl alcohol by heating to 50-55° C. The volume is reduce to about 22 L and cooled to 25-30° C. The solution is stirred for 5-6 hours. The resultant solid is collected and washed with cold ethyl alcohol. The filter cake is added to 50 L of water cooled to 10-15° C. Conc. HCl (0.97 L) is slowly added at 10-15° C.

to obtain a clear solution. The solution is filtered. The filtrate is slowly added to a solution of aqueous ammonia (0.79 L ammonia in 28 L water) at 10-25° C. The resulting mixture is stirred for 30 minutes and the solid is collected by centrifugation. The solid was dried at 45-50° C. until the moisture content was not more than 1.5%.

Example 9A

11-N-(3-amino-phenyl-1-ylmethyl-[1,2,3]-triazole-1-yl]butyl)-5-desosaminyl-3-oxo-2-fluoro-erythronolide A, 11,12-cyclic carbamate is optionally purified by dissolving material in a minimum amount of a solvent and adding an acid to the mixture to form a solid that precipitates from the solvent or precipitates after addition of a second solvent to the acidified mixture.

Example 10

Preparation of the 4-azido-butylamine. 1,4-Dibromobutane was dissolved in warm DMF and treated with sodium azide (three mole-equivalents). After the reaction was complete, the reaction mixture was diluted with water and the 1,4-diazido-butane was extracted into methyl t-butyl ether. Triphenylphosphine (1.08 mole-equivalents) was added the solution of 1,4-diazido-butane. When the reaction was complete the mixture was diluted with 5% hydrochloric acid until hydrolysis was complete. The acidic aqueous layer was separated, made basic with dilute sodium hydroxide. The resulting product was extracted into methylene chloride. The organic layer was separated and concentrated under reduced pressure to obtain the title material. The preparation of 1,4-diazido-butane is optionally performed with a mole-equivalent ratio to sodium azide of from about 1 to 3 to about 1 to 5. 1,4-Diazido-butane is optionally reduced to 4-azido-butylamine with other reducing agents, for example, sodium borohydride.

Comparative Example 1

The process described by Romero et al, in Tetrahedron letters, 46:1483-1487 (2005), for the preparation of macrolides is as follows:

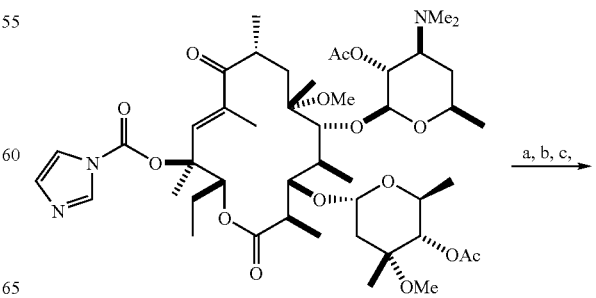

-continued

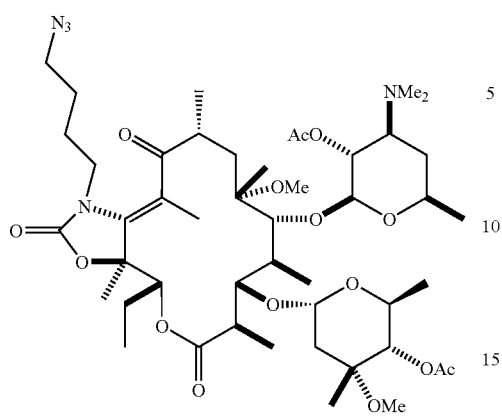

(a) 4-aminobutan-1-ol, DMF; (b) TsCl, pyridine; (c) NaN$_3$, DMF, 80° C. In this Example, the azide side chain is introduced by first reacting the activated acylated allylic alcohol at C-12 with 4-amino-1-butanol, subsequently activating the side chain hydroxyl group with tosyl chloride, and finally reacting with NaN$_3$ to prepare the corresponding side chain azide (see generally, US Patent Appl. Pub. No. 2006/0100164). This comparative process necessarily requires at least two steps to introduce the azide group onto the side chain.

Comparative Example 2

The process described by Liang et al. and Romero et al. (Tetrahedron letters, 46:1483-1487 (2005)) for the preparation of macrolides is as follows:

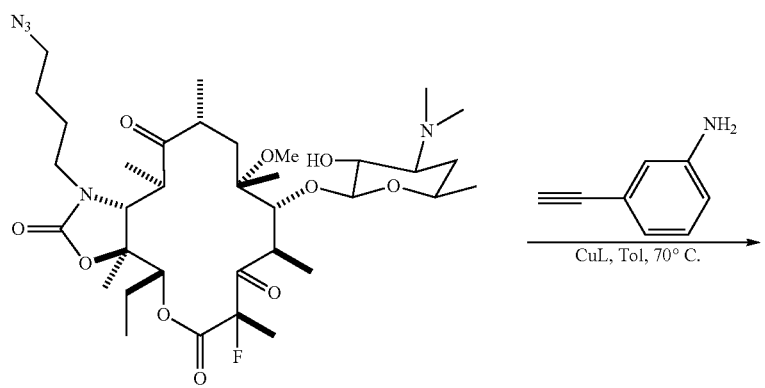

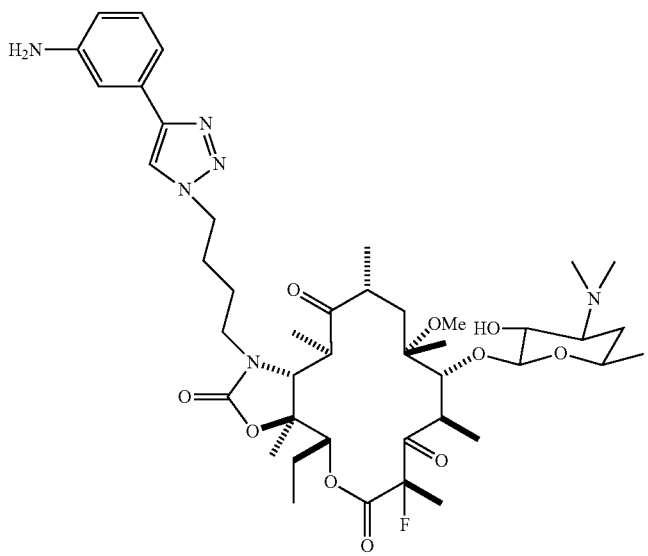

where the Huisgen reaction is performed on the unprotected desosamine. It was discovered that this lack of protection lead to the formation of side products. It was also surprisingly discovered that the reagent 3-aminophenylethyne was difficult to remove from the unprotected final product triazole. Further, it was discovered that conversion of the corresponding 2'-acetyl protected derivative to the 1,2,3-triazol in a Huisgen cyclization lead to concomitant acetyl migration from the desosamine sugar to the amino group of side chain aniline fragment, resulting in undesired product formation, correspondingly lower yields, and the need for subsequent purification steps.

What is claimed is:

1. A process comprising (c) reacting a compound of formula (V)

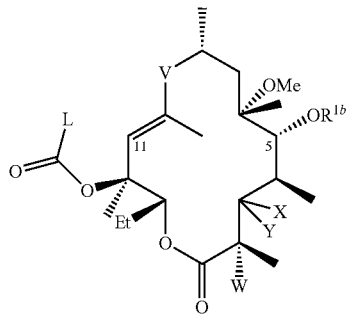

with a compound of formula $N_3$—B—A—$NH_2$ to obtain a compound of formula (VI)

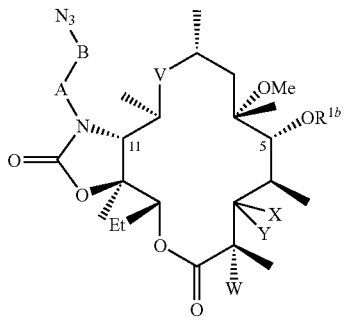

wherein:
$R^{1b}$ is a monosaccharide or disaccharide that includes a 2'-hydroxy group acylated with $R^{1a}$ wherein $R^{1a}$ is a sterically hindered acyl group; and L is a leaving group;
A is —$CH_2$—, —C(O)—, —C(O)O—, —C(O)NH—, —S(O)$_2$—, —S(O)$_2$NH—, —C(O)NHS(O)$_2$—;
B is —(CH$_2$)$_n$— where n is an integer ranging from 0-10, or B is an unsaturated carbon chain of 2-10 carbons;

V is —C(O)—, —C(=$NR^{11}$)—, —CH($NR^{12}R^{13}$)—, or —N($R^{14}$)CH$_2$—; where $R^{11}$ is hydroxy or alkoxy, $R^{12}$ and $R^{13}$ are each independently selected from the group consisting of hydrogen, hydroxy, alkyl, aralkyl, alkylaryl, alkoxy, heteroalkyl, aryl, heteroaryl, heteroarylalkyl, dimethylaminoalkyl, acyl, sulfonyl, ureyl, and carbamoyl; $R^{14}$ is hydrogen, hydroxy, alkyl, aralkyl, alkylaryl, alkoxy, heteroalkyl, aryl, heteroaryl, heteroarylalkyl, dimethylaminoalkyl, acyl, sulfonyl, ureyl, or carbamoyl;

W is hydrogen, F, Cl, Br, I, or OH; and

X is hydrogen; and Y is $OR^7$; where $R^7$ is hydrogen, a monosaccharide, a disaccharide, alkyl, aryl, heteroaryl, acyl, or —C(O)$NR^8R^9$, where $R^8$ and $R^9$ are each independently selected from hydrogen, hydroxy, alkyl, aralkyl, alkylaryl, heteroalkyl, aryl, heteroaryl, heteroarylalkyl, alkoxy, dimethylaminoalkyl, acyl, sulfonyl, ureyl, or carbamoyl; or X and Y taken together with the attached carbon to form C=O; and pharmaceutically acceptable salts, solvates, and hydrates thereof.

2. A process of claim 1, wherein V is C=O.

3. The process of claim 2 wherein -A-B— is alkylene.

4. The process of claim 2 wherein $R^{1b}$ is desosamine.

5. The process of claim 2 wherein $R^{1a}$ is selected from the group consisting of branched alkyl, aryl, heteroaryl, arylalkyl, and heteroarylalkyl acyl groups, each of which is optionally substituted.

6. The process of claim 4 wherein $R^{1a}$ is optionally substituted benzoyl.

7. The process of claim 2 wherein W is hydrogen or F.

8. The process of claim 2 wherein X is hydrogen; and Y is $OR^7$, where $R^7$ is cladinose.

9. The process of claim 1 wherein X and Y are taken together with the attached carbon to form C=O.

10. The process of claim 2 wherein $R^{1a}$ is benzoyl.

11. The process of claim 1 wherein $R^{1a}$ a is optionally substituted benzoyl, and further comprising converting the compound of formula (VI) into a compound of formula (I)

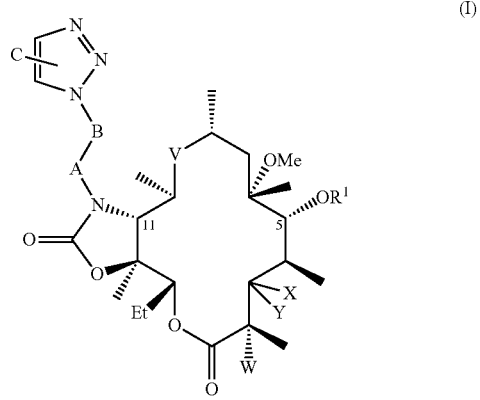

wherein

R[1] is a monosaccharide or disaccharide; and

C represents 1 or 2 substituents independently selected in each instance from the group consisting of hydrogen, halogen, hydroxy, alkyl, aralkyl, alkylaryl, alkoxy, heteroalkyl, aryl, heteroaryl, heteroarylalkyl, aminoaryl, alkylaminoaryl, acyl, acyloxy, sulfonyl, ureyl, and carbamoyl, each of which is optionally substituted.

12. The process of claim 11 wherein the compound of formula (I) is of the formula

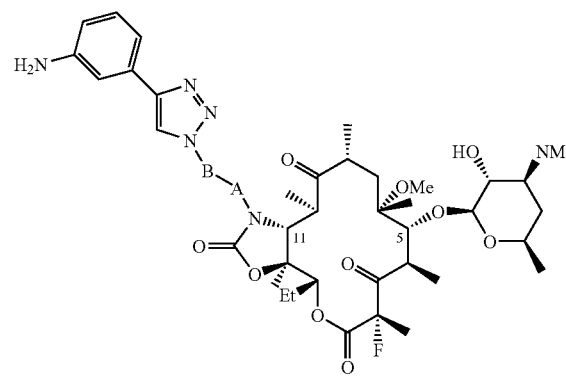

or a pharmaceutically acceptable salt thereof; where A is $CH_2$; and B is $(CH_2)_n$, and n is 3.

13. The process of claim 11 wherein V is C=O.

14. The process of claim 11 wherein X and Y are taken together with the attached carbon to form C=O.

15. The process of claim 11 wherein W is hydrogen or F.

16. The process of claim 11 wherein W is F.

17. The process of claim 11 wherein -A-B— is alkylene.

18. The process of claim 11 wherein C is optionally substituted aryl or optionally substituted heteroaryl.

19. The process of claim 11 wherein C is optionally substituted aryl.

20. The process of claim 11 wherein R[1] is a monosaccharide that includes a 2'-hydroxyl group acylated with R[1a].

21. The process of claim 20 wherein R[1a] is benzoyl.

22. The process of any one of claims 11 to 21 wherein R[1] is desosamine.

23. The process of claim 11 wherein the compound of formula (I) is of the formula

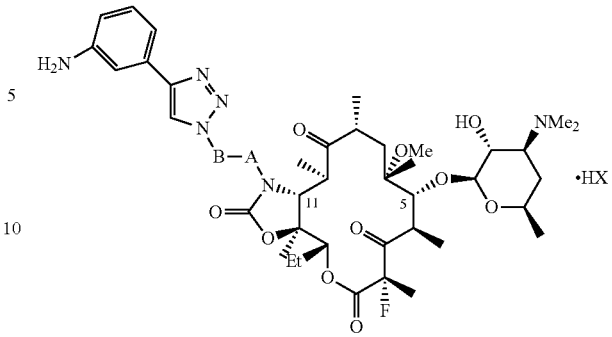

where A is $CH_2$; B is $(CH_2)_3$; and HX is an acid.

24. The process of claim 11 wherein the compound of formula (I) is of the formula

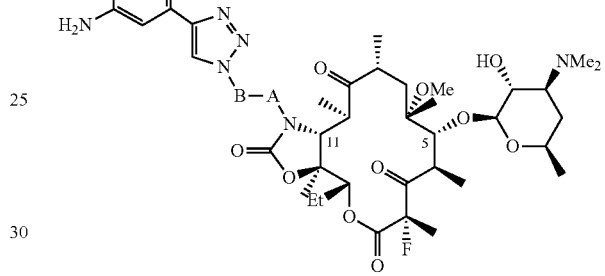

where A is $CH_2$; and B is $(CH_2)_3$.

25. The process of claim 11 wherein the compound of formula (I) is of the formula

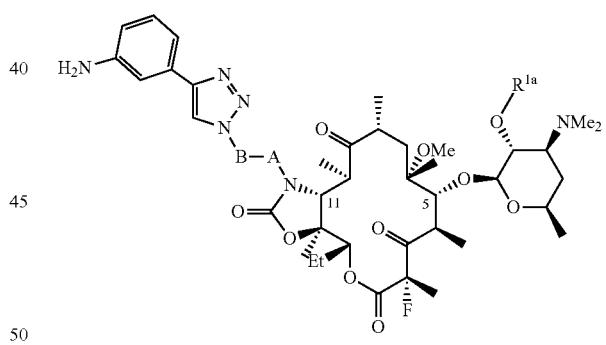

where A is $CH_2$; and B is $(CH_2)_3$.

* * * * *

UNITED STATES PATENT AND TRADEMARK OFFICE
CERTIFICATE OF CORRECTION

PATENT NO. : 9,453,042 B2
APPLICATION NO. : 12/739652
DATED : September 27, 2016
INVENTOR(S) : David E. Pereira Page 1 of 1

It is certified that error appears in the above-identified patent and that said Letters Patent is hereby corrected as shown below:

In the Claims

In Claim 5, Line 31, "The process of claim 2," should read -- The process of claim 4 --.
In Claim 9, Line 43, "The process of claim 1" should read -- The process of claim 2 --.
In Claim 12, Lines 31 and 32, "where A is CH2; and B is (CH2)n," should read -- where A is $CH_2$; and B is $(CH_2)_n$, --.

Signed and Sealed this
Twenty-first Day of March, 2017

Michelle K. Lee
*Director of the United States Patent and Trademark Office*